(12) United States Patent
Tanaka et al.

(10) Patent No.: US 12,036,068 B2
(45) Date of Patent: Jul. 16, 2024

(54) ULTRASONIC IMAGING DEVICE, TREATMENT SUPPORT SYSTEM, AND IMAGE PROCESSING METHOD

(71) Applicant: Hitachi, Ltd., Tokyo (JP)

(72) Inventors: Tomohiko Tanaka, Tokyo (JP); Ryo Imai, Tokyo (JP); Misaki Hiroshima, Tokyo (JP); Kenichi Kawabata, Tokyo (JP); Hiroshi Kuribara, Tokyo (JP)

(73) Assignee: FUJIFILM HEALTHCARE CORPORATION, Chiba (JP)

(*) Notice: Subject to any disclaimer, the term of this patent is extended or adjusted under 35 U.S.C. 154(b) by 207 days.

(21) Appl. No.: 17/416,707

(22) PCT Filed: Jan. 7, 2020

(86) PCT No.: PCT/JP2020/000128
§ 371 (c)(1),
(2) Date: Jun. 21, 2021

(87) PCT Pub. No.: WO2020/158301
PCT Pub. Date: Aug. 6, 2020

(65) Prior Publication Data
US 2021/0378632 A1 Dec. 9, 2021

(30) Foreign Application Priority Data
Jan. 31, 2019 (JP) .................. 2019-016072

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/4218* (2013.01); *A61B 8/445* (2013.01); *A61B 8/4494* (2013.01);
(Continued)

(58) Field of Classification Search
None
See application file for complete search history.

(56) References Cited

U.S. PATENT DOCUMENTS

| 6,336,899 B1 | 1/2002 | Yamazaki | |
| 6,425,865 B1* | 7/2002 | Salcudean | A61B 34/32 600/437 |

(Continued)

FOREIGN PATENT DOCUMENTS

| CN | 104640506 A | 5/2015 |
| CN | 105916446 A | 8/2016 |

(Continued)

OTHER PUBLICATIONS

Xia et al., "Fiber optic photoacoustic probe with ultrasonic tracking for guiding minimally invasive procedures," (Jul. 16, 2015), Proceedings vol. 9539, Opto-Acoustic Methods and Applications in Biophotonics II. (Year: 2015).*

(Continued)

*Primary Examiner* — Joel Lamprecht
*Assistant Examiner* — Ashish S Jasani
(74) *Attorney, Agent, or Firm* — MATTINGLY & MALUR, PC

(57) ABSTRACT

In a transcatheter treatment support technique using a combination of a guide wire equipped with a photoacoustic technique and an ultrasonic imaging device, the ultrasonic imaging device estimates a front edge position of the guide wire using a difference between arrival times of photoacoustic waves arriving at an array of elements configuring an ultrasonic probe or a change of an image of the photoacoustic generation source, which depends on a distance of the photoacoustic generation source from an imaging region, and grasps a relationship between an imaging position and the front edge position of the guide wire using the estimation result. This enables visually grasping a relationship between (Continued)

a region (imaging region) from which an image is able to be obtained with reflective waves from a biological body with use of the ultrasonic probe and an insertion object present outside the region, particularly, the front edge of the guide wire.

12 Claims, 17 Drawing Sheets

(51) Int. Cl.
*A61B 8/08* (2006.01)
*A61B 17/34* (2006.01)

(52) U.S. Cl.
CPC ............ *A61B 8/461* (2013.01); *A61B 8/5207* (2013.01); *A61B 8/54* (2013.01); *A61B 17/3403* (2013.01); *A61B 2017/3413* (2013.01)

(56) References Cited

U.S. PATENT DOCUMENTS

| | | | |
|---|---|---|---|
| 10,492,693 | B2 | 12/2019 | Irisawa |
| 2012/0253200 | A1 | 10/2012 | Stolka et al. |
| 2014/0094695 | A1* | 4/2014 | Jain ................ A61B 8/481 600/424 |
| 2015/0173723 | A1* | 6/2015 | Bates ................ A61B 8/585 600/424 |
| 2015/0297092 | A1 | 10/2015 | Irisawa |
| 2016/0038119 | A1* | 2/2016 | Desjardins .......... A61B 8/4444 600/424 |
| 2016/0120524 | A1 | 5/2016 | Suehira |
| 2016/0324423 | A1 | 11/2016 | Irisawa et al. |
| 2017/0245831 | A1 | 8/2017 | Nishigaki et al. |
| 2020/0008782 | A1* | 1/2020 | Miyachi ................ A61B 8/463 |
| 2020/0037983 | A1* | 2/2020 | Poland .................. A61B 8/14 |
| 2022/0346752 | A1* | 11/2022 | Van De Pas ......... A61B 8/4254 |

FOREIGN PATENT DOCUMENTS

| | | |
|---|---|---|
| JP | 2000185041 A | 7/2000 |
| JP | 2009-095379 A | 5/2009 |
| JP | 2013-511355 A | 4/2013 |
| JP | 2015-01630 A | 1/2015 |
| JP | 2015-16300 A | 1/2015 |
| JP | 2015037519 A | 2/2015 |
| JP | 2015100546 A | 6/2015 |
| JP | 2015-139465 A | 8/2015 |
| JP | 2017-148407 A | 8/2017 |
| WO | 2018146929 A1 | 8/2018 |

OTHER PUBLICATIONS

Xia et al., "Ultrasonic Needle Tracking with a Fibre-Optic Ultrasound Transmitter for Guidance of Minimally Invasive Fetal Surgery," (Sep. 4, 2017), Med Image Comput Comput Assist Interv. Sep. 2017; 10434: 637-645. (Year: 2017).*
Xia et al., "Looking beyond the imaging plane: 3D needle tracking with a linear array ultrasound probe," (Jun. 16, 2017), Scientific Reports vol. 7, Article No. 3674 (2017). (Year: 2017).*
Lediju et al., "Photoacoustic-based visual servoing of a needle tip," (Oct. 19, 2018), Scientific Reports, (2018) 8:15519. (Year: 2018).*
International Search Report of PCT/JP2020/000128 dated Mar. 17, 2020.
International Preliminary Report received in corresponding International Application No. PCT/JP2020/000128 dated Jul. 27, 2021.
Translation of Written Opinion received in corresponding International Application No. PCT/JP2020/000128 dated Mar. 17, 2020 .
Japanese Office Action received in corresponding Japanese Application No. 2019-016072 dated Feb. 22, 2022.
Chinese Office Action received in corresponding Chinese Application No. 202080005549.3 dated Oct. 31, 2023.
Chinese Office Action received in corresponding Chinese Application No. 202080005549.3 dated Mar. 28, 2024.

* cited by examiner

FIG. 10
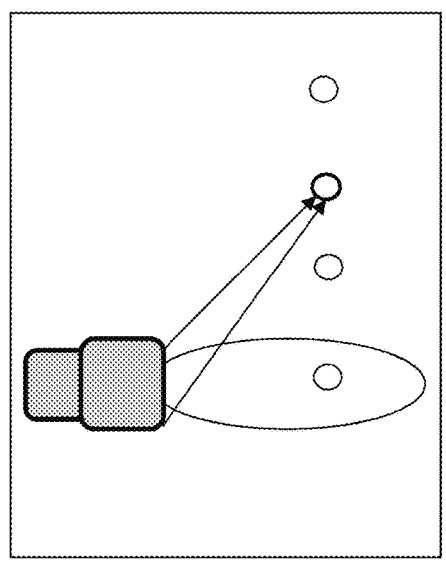
(a)
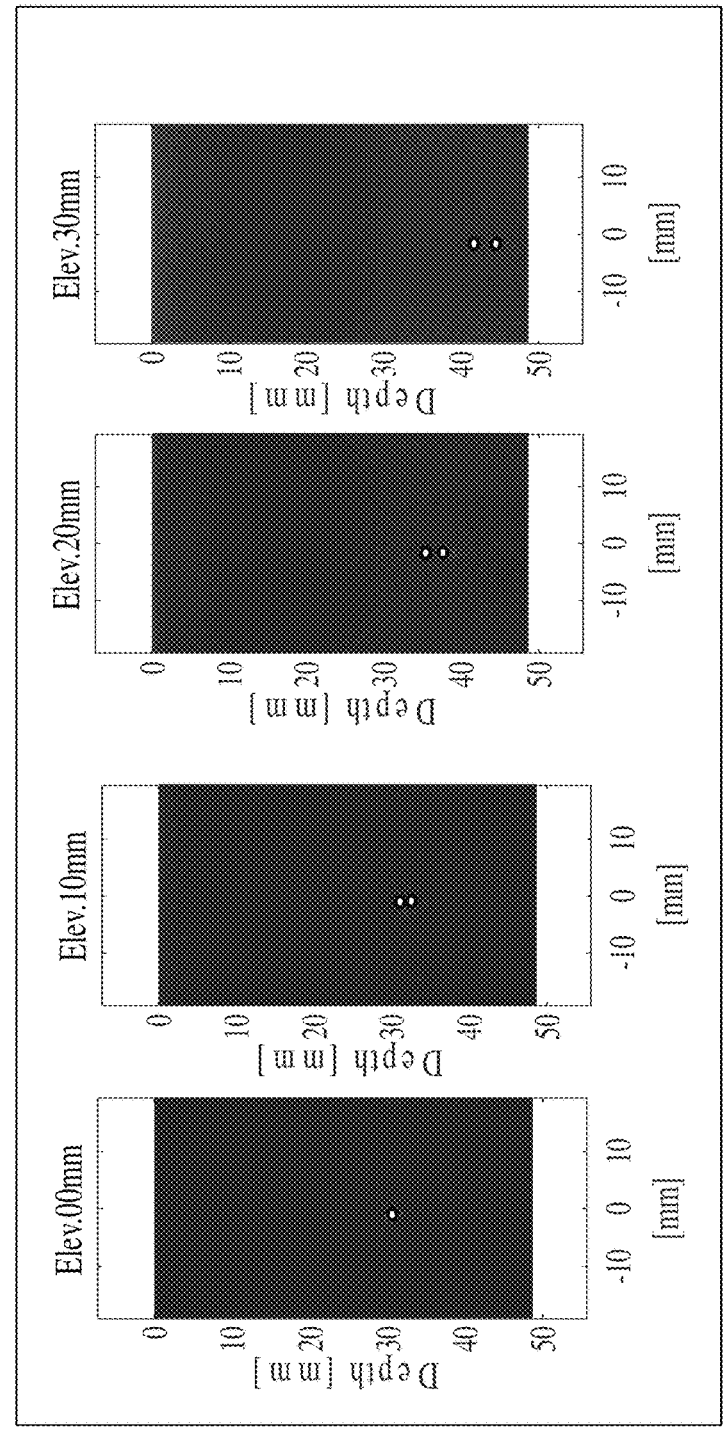
(b)

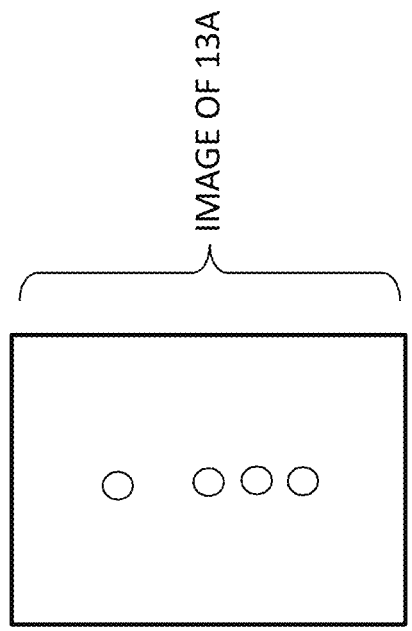
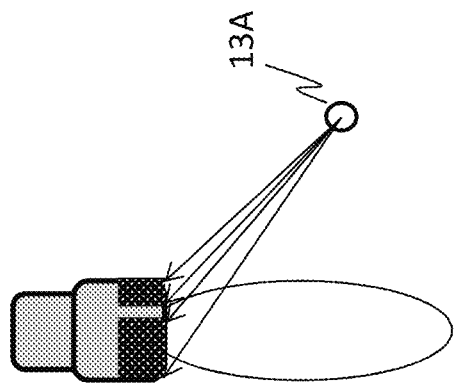
FIG. 12

ULTRASONIC IMAGING DEVICE, TREATMENT SUPPORT SYSTEM, AND IMAGE PROCESSING METHOD

TECHNICAL FIELD

The present invention relates to a technique to provide a support using an ultrasonic imaging device in inserting a guide wire with an ultrasonic wave generation source for, for example, photoacoustic imaging mounted thereon into the body.

BACKGROUND ART

Transcatheter treatment is one type of therapy in which the burden on patients is smaller as compared with surgeries such as thoracotomy, and is, therefore, widely used for treatment mainly for, for example, angiostenosis. In transcatheter treatment, grasping a relationship between a region serving as a therapeutic objective and a catheter is important, and, as an imaging method for supporting such grasping, X-ray fluoroscopy is currently used. While there is an attempt at using an ultrasonic image as a supporting image, it is not easy to extract the front edge of a guide wire by ultrasonic waves, so that such an attempt has not lead to widespread use.

On the other hand, with regard to puncture needles, there is also proposed a technique of mounting, on a puncture needle, a photoacoustic technique for generating a photoacoustic signal from the front edge of the needle and detecting the photoacoustic signal with an ultrasonic probe included in an ultrasonic imaging device, thus detecting the position of the needle front edge (Patent Literature 1 and Patent Literature 2).

Specifically, Patent Literature 1 discloses a technique of radiating laser light from a pulsed laser generation source onto a needle, detecting photoacoustic waves generated from the front edge of the needle by light propagated through the needle with an ultrasonic probe included in an ultrasonic imaging device, and thus extracting the detected photoacoustic waves as a photoacoustic image. Patent Literature 2 discloses a technique of acquiring a photoacoustic image while changing the orientation of an ultrasonic probe, determining whether a position (orientation) of the ultrasonic probe where a signal becomes strongest and a position of the ultrasonic probe in imaging using an ultrasonic imaging device (imaging in a normal mode) coincide with each other, and thus enabling grasping a relationship of the needle front edge relative to an ultrasonic image (for example, a B-mode image).

PRIOR ART LITERATURE

Patent Literature

Patent Literature 1: JP-T-2013-511355 (the term "JP-T" as used herein means a published Japanese translation of a PCT application.)
Patent Literature 2: JP-A-2015-139465

DISCLOSURE OF THE INVENTION

Problems that the Invention is to Solve

The technique described in Patent Literature 2 is able to determine whether the front edge of an insertion object (puncture needle) is present immediately below an ultrasonic probe and is thus able to enable knowing that the needle front edge depicted on an displayed ultrasonic image is actually present at a mismatched position or knowing the direction of mismatching, but is unable to enable visually grasping a relationship between a therapeutic objective region and a position where the front edge of the insertion object is actually present. Moreover, this technique essentially requires performing imaging in a peak search mode, which acquires a plurality of photoacoustic images while changing the orientation of the ultrasonic probe, and is not able to display an ultrasonic image (captured in the normal mode) at a high time resolution.

In the case of inserting, for example, a catheter into an object under examination, to enable concentrating on catheter insertion work while viewing an image, it is desirable that operations required for imaging (operations on the probe) be as few as possible and a positional relationship between a target for treatment and a therapeutic tool be successively grasped in a good visibility.

The present invention is directed to an issue of providing a technique to enable visually readily grasping a relationship between a region from which an image is able to be obtained based on reflective waves reflected from a biological body (imaging region) and an insertion object present outside the region, particularly, the front edge of a guide wire using an ultrasonic probe.

Means for Solving the Problems

To solve the above-mentioned issue, in a transcatheter treatment support technique using a combination of a guide wire with an ultrasonic wave generation source mounted thereon and an ultrasonic imaging device, the present invention estimates a front edge position of the guide wire using a difference between arrival times of ultrasonic waves (ultrasonic waves generated from the ultrasonic wave generation source) arriving at an array of elements configuring an ultrasonic probe or an image of the ultrasonic wave generation source, which depends on a distance of the ultrasonic wave generation source from an imaging region, and grasps a relationship between an imaging position and the front edge position of the guide wire using a result of such estimation.

Thus, an ultrasonic imaging device according to the present invention includes an imaging unit that transmits a beam-formed ultrasonic signal to an object under examination via an ultrasonic probe, receives a reflective ultrasonic signal from a region to which the ultrasonic signal is radiated, and captures an ultrasonic image of a diffracted wave region, which is determined by the radiated region, and an ultrasonic signal analysis unit that receives, via the ultrasonic probe, ultrasonic waves generated from an ultrasonic wave generation source inserted into an inside of the object under examination and analyzes the received ultrasonic waves, wherein the ultrasonic signal analysis unit estimates a position of the ultrasonic wave generation source present at a position deviating from the diffracted wave region with use of a difference between receiving times or arrival clock times of ultrasonic waves which a plurality of elements configuring the ultrasonic probe respectively receives (ultrasonic waves generated from the ultrasonic wave generation source).

Moreover, a treatment support system according to the present invention is characterized by including an ultrasonic imaging device including an imaging unit that transmits a beam-formed ultrasonic signal to an object under examination via an ultrasonic probe, receives a reflective ultrasonic signal from a region onto which the ultrasonic signal has been radiated, and captures an ultrasonic image of the region, and a photoacoustic device including an ultrasonic wave generation source fixed to a therapeutic tool, which is configured to be inserted into an object under examination, a light generation unit that generates a light signal for causing the ultrasonic wave generation source to generate an ultrasonic signal, a light guide path that guides the light signal from the light generation unit to the photoacoustic generation source, wherein the ultrasonic imaging device further includes an ultrasonic signal analysis unit that receives, via the ultrasonic probe, ultrasonic waves generated from the ultrasonic wave generation source inserted into an inside of the object under examination and analyzes the received ultrasonic waves, and wherein the ultrasonic signal analysis unit estimates a position of the ultrasonic wave generation source present at a position deviating from the region with use of a difference between receiving times (arrival clock times) of ultrasonic waves which a plurality of elements configuring the ultrasonic probe respectively receives.

Advantage of the Invention

According to the present invention, using a time difference between ultrasonic waves arriving at an array of elements enables calculating a geometric positional relationship between the array of elements and an ultrasonic wave generation source, and this enables grasping a position of the front edge of an insertion object present outside a region onto which an ultrasonic signal is radiated from the array of elements. Moreover, such positional information can be obtained in a short amount of time after generation of ultrasonic waves, and is, therefore, able to be displayed on an image which is being captured.

BRIEF DESCRIPTION OF THE DRAWINGS

FIGS. 10(a) and 10(b) are diagrams used to explain processing which an analysis unit performs in a third embodiment, in which FIG. 10(a) is a diagram illustrating positions of an ultrasonic wave generation source relative to a diffracted wave region and FIG. 10(b) is a diagram illustrating images of the ultrasonic wave generation source in the respective positions.

FIG. 12 is a diagram illustrating an example of an image of an ultrasonic wave generation source which is acquired in the modification example of the third embodiment.

MODE FOR CARRYING OUT THE INVENTION

Embodiments of an ultrasonic imaging device and a transcatheter treatment support system (hereinafter abbreviated as a "support system") according to the present invention are described as follows.

Figure 1:
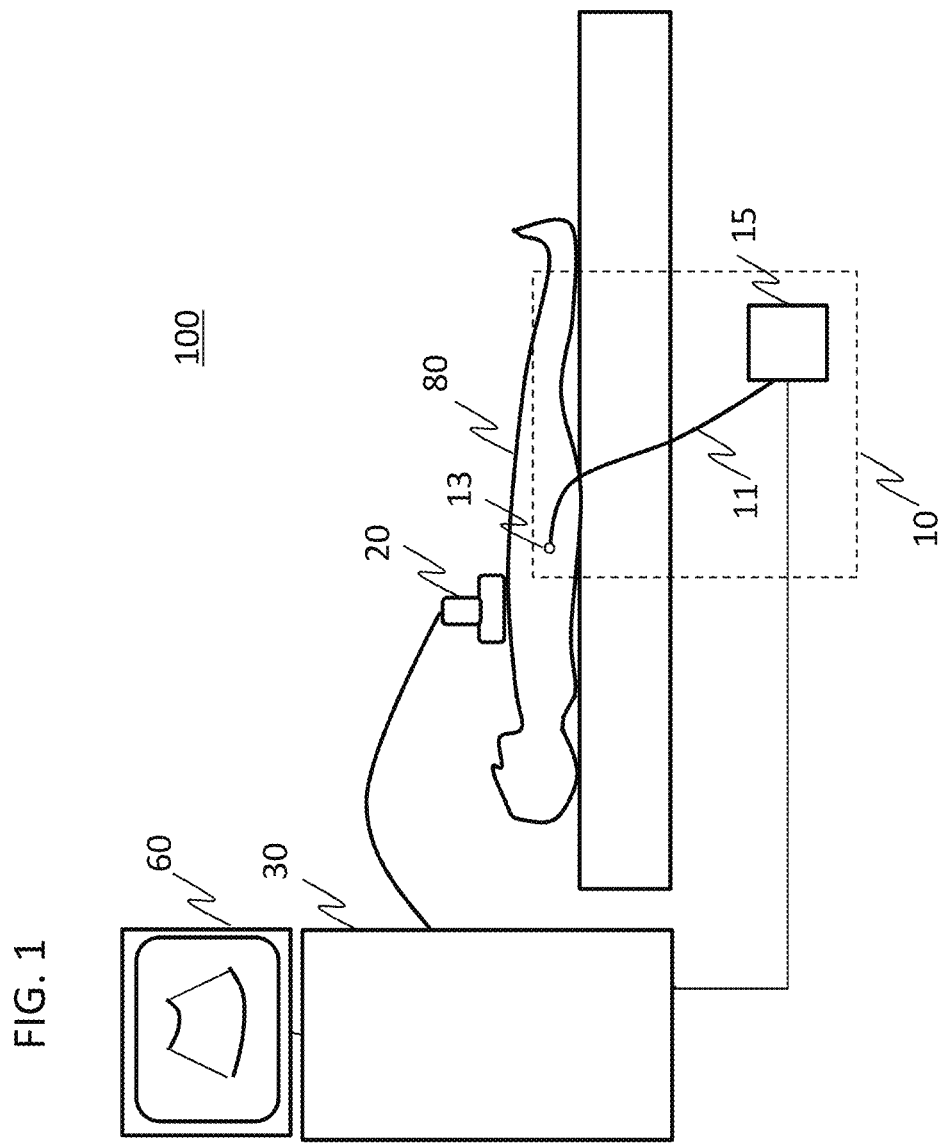
FIG. 1 is a diagram illustrating an overall outline of an embodiment of a treatment support system according to the present invention.

First, an overall outline of the support system is described with reference to FIG. 1. As illustrated in FIG. 1, a support system 100 according to the present embodiment includes a biological body insertion tool 11 with an ultrasonic wave generation device 10 mounted thereon and an ultrasonic probe 20, and includes an ultrasonic imaging unit 30, which acquires an ultrasonic image of an object under examination 80 into which the biological body insertion tool has been inserted, and a display unit 60 for the ultrasonic imaging unit 30.

Figure 2:
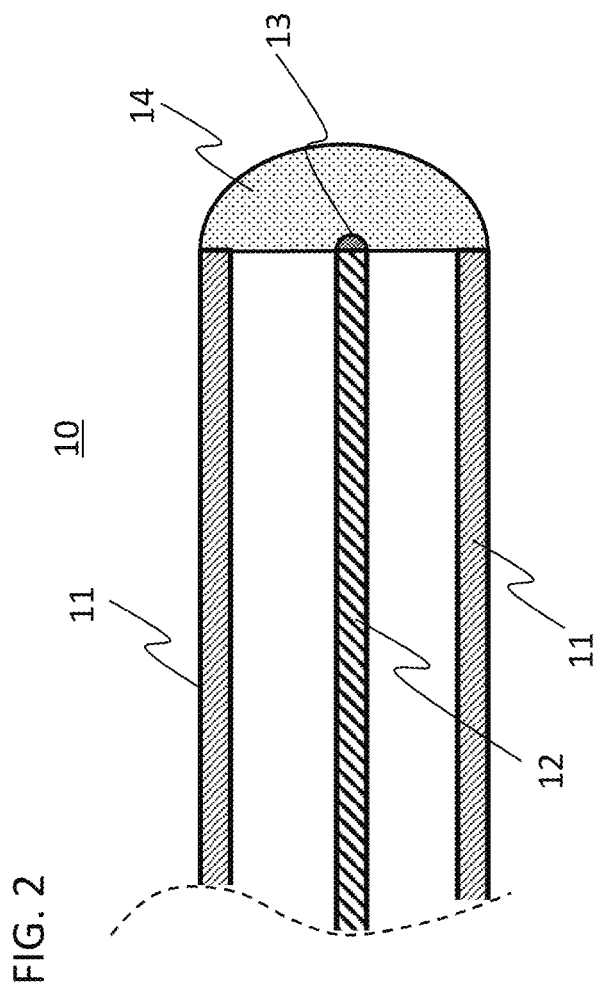
FIG. 2 is a diagram illustrating a partial cross section of an ultrasonic source-mounted wire.

The biological body insertion tool 11 is, for example, a therapeutic instrument, such as a balloon catheter or a micro-catheter, or a guide wire for conveying such a therapeutic instrument to a target site. In the present embodiment, a case where, for example, the biological body insertion tool is a guide wire is described. While, in the following embodiment, a case where the ultrasonic wave generation device 10 is a photoacoustic signal (hereinafter referred to as a "PA signal") generation source, which generates a PA signal, is described as an example, a piezoelectric element can be used as the ultrasonic wave generation device 10 with respect to the purpose of generating ultrasonic waves. As illustrated in FIG. 2, the ultrasonic wave generation device 10 includes an optical fiber 12, which is arranged inside a hollow portion of the guide wire 11, which is flexible and hollow, an ultrasonic wave generation source (PA signal generation source) 13, which is fixed to an insertion-side end surface of the optical fiber 12, and a light generation unit 15, which is connected to the other end of the optical fiber 12 (an end portion opposite to the end portion where the ultrasonic wave generation source 13 is fixed) and generates laser light, and the optical fiber 12 functions as a light guide member for guiding laser light generated by the light generation unit 15 to the ultrasonic wave generation source 13, which is mounted at the front edge of the optical fiber 12. The ultrasonic wave generation device 10 including these members is referred to as a "photoacoustic source-mounted wire" with inclusion of the guide wire 11, which is hollow.

The PA signal generation source 13 is made from a material which emits ultrasonic waves, such as a PA signal, by being adiabatically expanded upon reception of laser light, such as a known pigment (photosensitizer), metallic nanoparticles, or a carbon-based compound. The front edge of the optical fiber 12, which includes the PA signal generation source 13, is covered with a plastic sealing member 14. Furthermore, while, in FIG. 2, the PA signal generation source 13 is located at the front edge of the wire 11, such location is not limited to the wire front edge.

Figure 3:
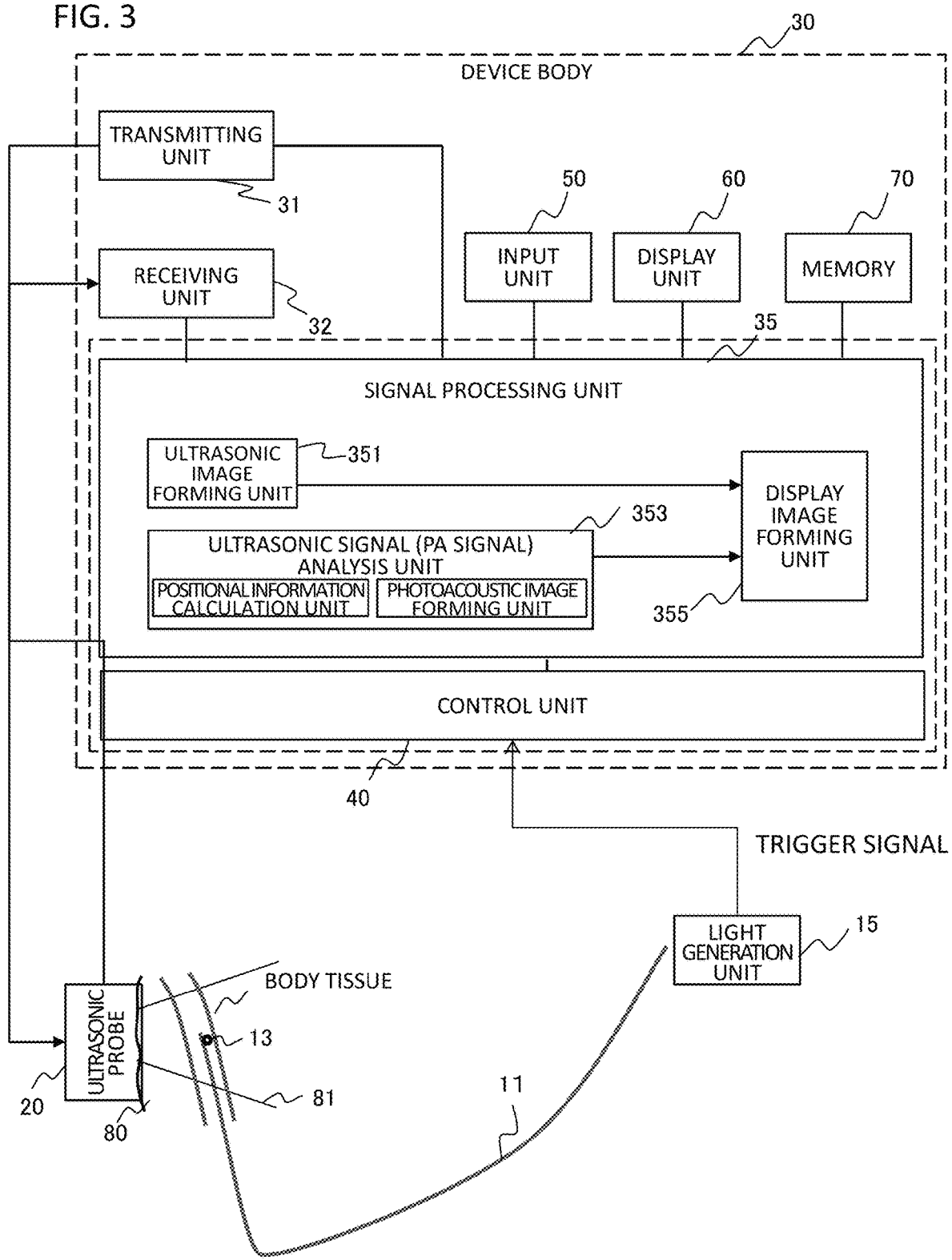
FIG. 3 is a diagram illustrating the details of an ultrasonic imaging unit (ultrasonic imaging device) of the treatment support system illustrated in FIG. 1.

The ultrasonic imaging unit 30 has a configuration similar to that of a general ultrasonic imaging unit except that a function of processing a PA signal (an ultrasonic signal analysis unit) is added thereto, and, as illustrated in FIG. 3, includes a transmitting unit 31, which transmits an ultrasonic signal to the ultrasonic probe 20, a receiving unit 32, which receives reflective waves (an RF signal) detected by the ultrasonic probe 20 and performs processing, such as phasing and addition, on the reflective waves, and a signal processing unit 35, which performs processing of the RF signal received by the receiving unit 32. Moreover, the ultrasonic imaging unit 30 includes a control unit 40, which controls the ultrasonic imaging unit 30 and its accessory equipment and controls the photoacoustic device 10 as needed, an input unit 50, which is used for a user to input conditions and commands required for performing imaging, the display unit 60, which displays, for example, an ultrasonic image acquired by the ultrasonic imaging unit 30 or a graphical user interface (GUI), and a memory 70, which stores, for example, an image that is a result of processing performed by the signal processing unit 35.

The signal processing unit 35 includes an ultrasonic image forming unit 351, which generates an ultrasonic image such as a B-mode image using an RF signal, which is reflective waves, an ultrasonic signal analysis unit (PA signal analysis unit) 353 (hereinafter referred to simply as "analysis unit"), which detects a PA signal emitted from the PA signal generation source 13 and detected by each transducer element of the ultrasonic probe 20 and estimates information about the position of the PA signal generation source 13, and a display image forming unit 355, which generates an image to be displayed on the display unit 60. The ultrasonic image forming unit 351 can have the function of generating, in addition to an ultrasonic image of an object under examination, such as a B-mode image, an image of the PA signal generation source 13 (photoacoustic image) using a PA signal. The analysis unit 353 estimates the position and direction (collectively referred to as "positional information") of the PA signal generation source 13.

A part or the whole of functions of the units constituting the signal processing unit 35 and the control unit 40 is able to be implemented by uploading software obtained by programming the functions onto a calculator including a CPU or GPU and a memory. Moreover, a part or the whole of functions of the units is able to be implemented by hardware, such as an electronic circuit, ASIC, or FPGA. Furthermore, the control unit 40 can be configured with a calculator different from a calculator used for the signal processing unit 35.

The ultrasonic probe 20 can be configured with any one of a variety of ultrasonic probes 20 including, for example, a 1D array probe, which includes a large number of transducer elements arranged in a one-dimensional direction, a 1D 3-arrangement probe, which includes two or three rows of array arrangements in a direction perpendicular to the array arrangement direction of the 1D array probe, and a 2D array probe, which includes a large number of array arrangements in two-dimensional directions. The analysis unit 353 can employ an analytical method corresponding to a type of ultrasonic probe to be used.

Next, the outline of an operation of the ultrasonic wave generation device having the above-mentioned configuration is described. Here, the case of, while performing ordinary ultrasonic imaging, inserting a guide wire with the photoacoustic device 10 mounted thereon, which guides, for example, a catheter into the body of an object under examination and monitoring the front edge position of the guide wire using a PA signal is described. Ordinary imaging is referred to as "imaging mode" and monitoring using a PA signal is referred to as "PA analysis mode".

An operation in the imaging mode is similar to that of a conventional ultrasonic imaging device, and includes transmitting ultrasonic waves from the transmitting unit 31 via the ultrasonic probe 20 and receives, at the ultrasonic probe 20, reflective waves obtained by the transmitted ultrasonic waves reflecting from tissues of the inside of the object under examination. The receiving unit 32 performs processing, such as phasing and addition, on a received signal received for each frame and sends the processed signal to the signal processing unit 35. In a case where a 2D ultrasonic probe 20 is used, information corresponding to the strength of reflective waves in three-dimensional directions obtained by combining two-dimensional directions and a depth direction can be obtained. The ultrasonic image forming unit 351 of the signal processing unit 35 generates an ultrasonic image, such as a B-mode image, using a frame signal received from the receiving unit 32, and passes the generated ultrasonic image to the display image forming unit 355. The display image forming unit 355 displays a B-mode image together with ancillary information thereabout on the display unit 60.

Figure 4:
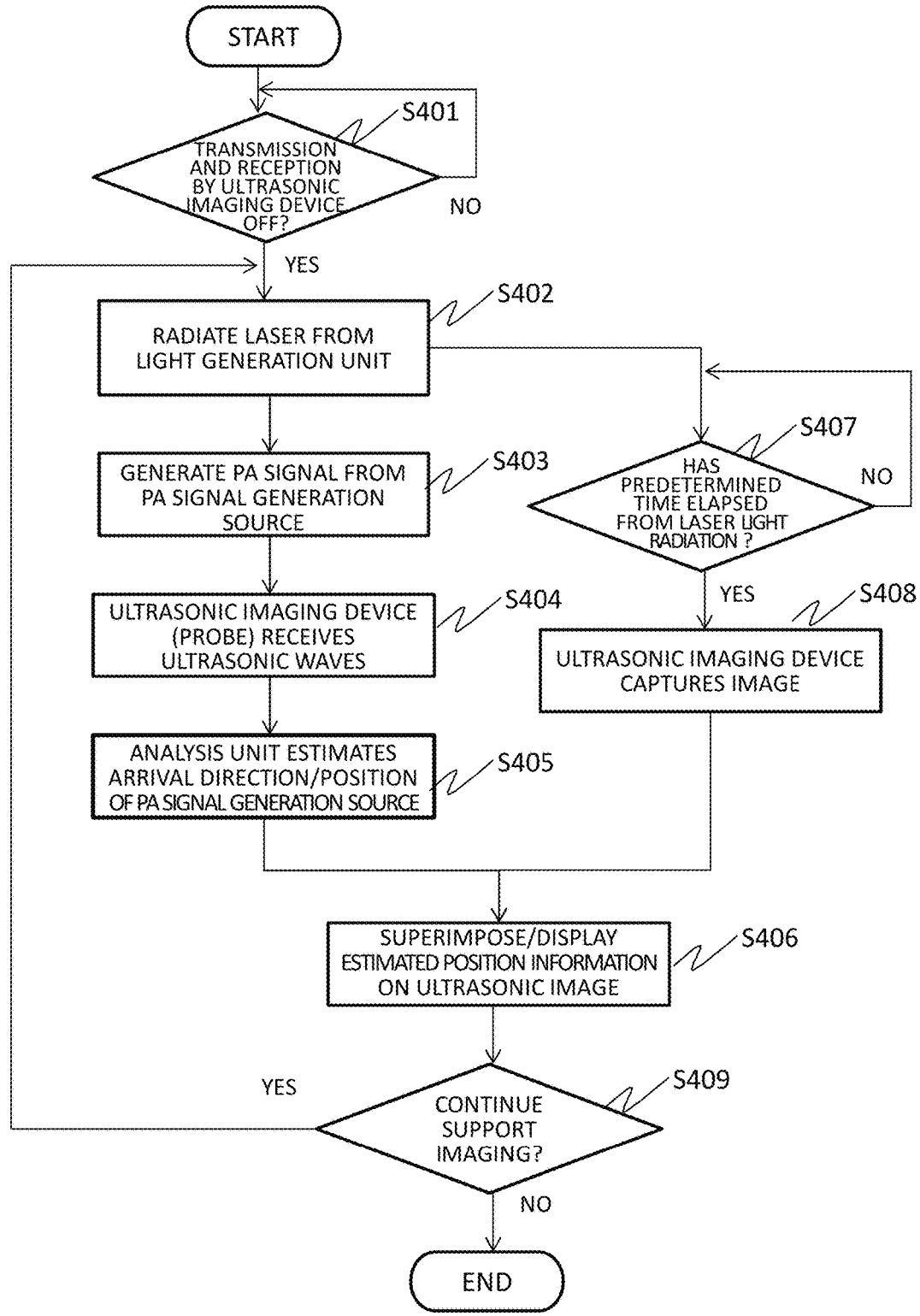
FIG. 4 is a chart illustrating a flow of operations at the time of imaging and ultrasonic signal analysis.

On the other hand, in the PA analysis mode, as illustrated in FIG. 4, while a catheter is inserted into the body of an object under examination, for example, into a blood vessel thereof, the operation of the transmitting unit 31 is temporarily stopped (S401), and the light generation unit 15 is caused to operate, so that pulsed laser light is radiated from the light generation unit 15 (S402). When light emitted by the light generation unit 15 is radiated onto the PA signal generation source 13 via the optical fiber 12 of the guide wire 11 inserted into the body, a PA signal (ultrasonic waves) is generated from a photoacoustic material configuring the PA signal generation source 13 (S403), and the generated PA signal is detected by each element of the ultrasonic probe 20 (S404).

Figure 5:
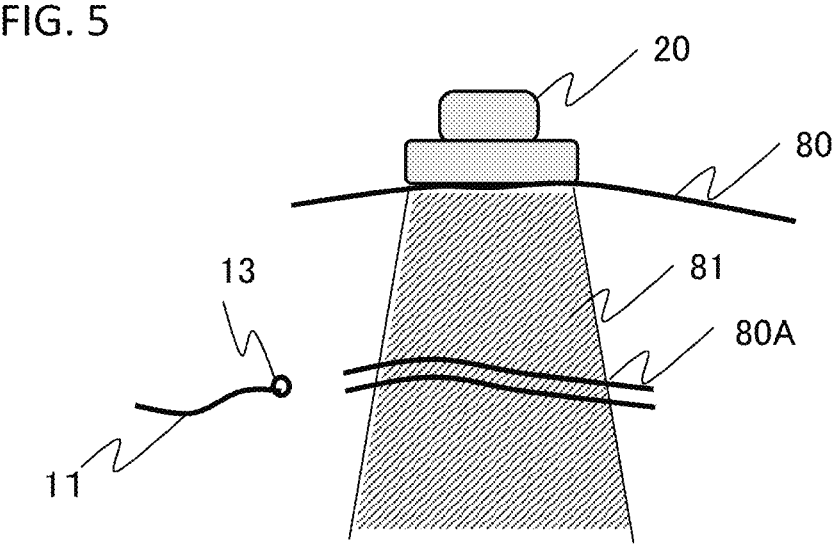
FIG. 5 is a diagram used to explain a relationship between an imaging region and an ultrasonic wave generation source.

As illustrated in FIG. 5, an ultrasonic signal which is received by the ultrasonic probe 20 is reflective waves reflected from an object-under-examination tissue 80A present in a range (range indicated by hatching) into which an ultrasonic beam radiated from the ultrasonic probe 20 expands by being beam-formed, and the inside of the range is an imaging region 81. Thus, the imaging region 81 is a region to which diffracted waves are spherically propagated from each element of the probe array, and is here also referred to as a "diffracted wave region". A time taken for reflective waves from the diffracted wave region 81 to arrive at the probe array almost depends on the depth. On the other hand, a PA signal from the PA signal generation source 13 is not reflective waves but a signal which directly arrives at each element of the probe array, and a time duration taken from the time of generation of a photoacoustic signal in the PA signal generation source 13 to the time of detection thereof by each element is proportional to a distance between the PA signal generation source 13 and each element.

Here, assuming that the position of the PA signal generation source 13 deviates to the outer side of the diffracted wave region with respect to the lateral direction (the arrangement direction of elements) of the ultrasonic probe 20, a time difference occurs between times taken for the PA signal to arrive at the respective elements.

The receiving unit 32 passes PA signals detected by the respective elements with a time difference included thereinto the analysis unit 353 without performing processing such as phasing on the PA signals. The analysis unit 353 estimates positional information about the PA signal generation source 13 using information concerning the PA signals detected by the respective elements and the receiving times (arrival times of PA signals) for the respective elements (S405).

The display image forming unit 355 receives information concerning the position of the PA signal generation source 13 from the analysis unit 353, generates a display image obtained by superimposing the received information on a B-mode image or a display image indicating the received information as additional information, and displays the generated display image on the display unit 60 (S406). The way of displaying positional information on the display unit 60 includes various modes, which are described in embodiments described below.

After a predetermined waiting time after radiation of laser light from the light generation unit 15, the transmitting unit 31 resumes ultrasonic wave transmission (measurement in the imaging mode), which has been stopped, (S407 and S408), and displays the acquired ultrasonic image on the display unit 60. The waiting time required for resuming the imaging mode only needs to be a time required for detection of a photoacoustic signal by the ultrasonic probe 20 and analysis thereof by the analysis unit 353, and the control unit 40 is able to resume the imaging mode with a predetermined waiting time in response to radiation of light in the light generation unit 15 set as a trigger signal.

Such imaging operations in the imaging mode and the analysis mode are repeated a plurality of times until, for example, the front edge of the guide wire penetrates into the diffracted wave region or arrives at a target position (S409). While such switching of modes is performed under the control of the control unit 40, adjustment by the user can be received via the input unit 50 as appropriate.

Furthermore, while, in the analysis mode, only an analysis using a PA signal is assumed to be performed, the ultrasonic image forming unit 351 can be configured to process a PA signal as with an ultrasonic reflective signal in the imaging mode and thus generate an image of the PA signal generation source 13 (referred to as a "PA image"). This image is an image in which only the PA signal generation source 13 has luminance information, and the position of the PA signal generation source 13 becomes a position relatively deep in depth of the diffracted wave region. The PA image can be displayed together with a B-mode image, and the analysis unit 353 can use information about the PA image for position estimation.

According to the ultrasonic imaging device in the present embodiment, while performing imaging of a target site, monitoring the position of the front edge of a guide wire for guiding a catheter in an analysis mode which is effected during imaging of the target site and displaying information about the monitored position on an ultrasonic image acquired in an imaging mode are executed, and it enables a user to check, on the ultrasonic image, a way in which the guide wire comes close to a site serving as an imaging target.

Next, various embodiments of a method of analyzing the position of the PA signal generation source 13 in the analysis unit 353 and a display method for a result of analysis are described. In each embodiment, configurations of the ultrasonic imaging device and signal processing to be performed thereby are similar unless otherwise stated, and the configuration illustrated in FIG. 3 is referred to as appropriate.

First Embodiment

In the present embodiment, the analysis unit 353 estimates a distance in the lateral direction of the ultrasonic wave generation source 13 using a time difference between arrival times of ultrasonic waves (beacon ultrasonic signals) emitted from the ultrasonic wave generation source 13 detected by the respective elements of a 1D array probe 20A. Even in the present embodiment, a case where ultrasonic waves emitted by the ultrasonic wave generation source 13 are a PA signal is described as an example.

As illustrated in FIG. 5, in a case where the guide wire 11 is inserted into the blood vessel (80A) and advanced to a treatment site (target), when imaging is performed with a plane taken along running of the blood vessel set as an imaging cross section, the guide wire comes to proceed to an imaging region from any one of the right and left sides of the imaging region. Accordingly, estimating the distance in the lateral direction enables knowing how the guide wire has come close to the target.

An arrival time taken for a PA signal emitted from the PA signal generation source 13 to arrive at each element of the ultrasonic probe is proportional to a distance between the PA signal generation source 13 and each element. The arrival time is a time from the clock time of generation of a PA signal to the clock time of reception thereof by each element, and, if the PA signal generation clock time is found, the arrival time is able to be calculated from information about the receiving clock time at which the receiving unit 32 received the PA signal. Since the clock time at which the PA signal was emitted from the PA signal generation source 13 is able to be regarded as the same as the clock time at which laser light was emitted from the light generation unit 15, in a case where, at the time of generation of laser light, a trigger signal for ultrasonic wave transmission is sent from the light generation unit 15 to the control unit 40, the laser generation clock time, i.e., the PA signal generation clock time, is able to be calculated from the clock time at which the trigger signal was received.

Moreover, when the light generation unit 15 radiates pulsed laser light, the control unit 40 can receive pulse generation timing to obtain the PA signal generation clock time.

The analysis unit 353 calculates the position (xc, yc) of the PA signal generation source 13 from the ultrasonic probe (the respective elements thereof) based on the PA signal generation clock time by using the following formulae (1) and (2). Symbol "xc" denotes the distance in the lateral direction of the ultrasonic probe, symbol "yc" denotes the distance in the depth direction of the ultrasonic probe, and the center position of the array is assumed to be an origin.

$$x_c = \frac{1}{N}\sum_n^N\left(x_n - \frac{C^2}{4\delta x}(t_{n+1}^2 - t_{n-1}^2)\right) \quad (1)$$

-continued $$y_c = \sqrt{\frac{1}{N}\sum_{n=1}^{N} C^2(t_n)^2 - (x_n - x_c)^2} \quad (2)$$

In the above formulae, symbol N denotes the number of elements of the 1D array, symbol "n" denotes any integer of 1 to N, symbol "xn" denotes the coordinates of the n-th element, symbol "tn" denotes the arrival time taken to arrive at the n-th element, symbol "δx" denotes the calculation lattice spacing (which can be an interval between adjacent elements), and symbol C denotes the speed of sound.

The positional information calculated in the above-mentioned way is stored in, for example, the memory 70 and, at the same time, is displayed on the display unit 60 together with an ultrasonic image (B-mode image) formed by the ultrasonic image forming unit 351. Moreover, when repeatedly executing the analysis mode, the analysis unit 353 updates positional information stored in the memory 70 and positional information which is displayed, for every execution of repetition. This enables the user to, while fixing the ultrasonic probe 20 to a position available for imaging of an intended treatment site (in other words, while, without the need for the movement of the ultrasonic probe 20 to detect the front edge of the guide wire, constantly performing imaging of a target site), proceed with manipulation while confirming, on a displayed image, the front edge position, which occasionally changes from moment to moment due to penetration by the guide wire.

Furthermore, in a case where the PA signal generation source 13 deviates not only in the lateral direction but also in the elevation direction (a direction perpendicular to the arrangement direction of the array) with respect to the diffracted wave region (imaging plane), it is impossible to calculate an accurate position in the lateral direction only by using formulae (1) and (2). However, as long as the array arrangement direction of the ultrasonic probe almost coincides with the running direction of the blood vessel, the front edge of the guide wire moving on to a target does not deviate to a large extent in the elevation direction. Therefore, the positional information calculated in formulae (1) and (2) is sufficiently helpful to a guide support as information for knowing how the front edge of the guide wire has come close to the target.

Figure 6:
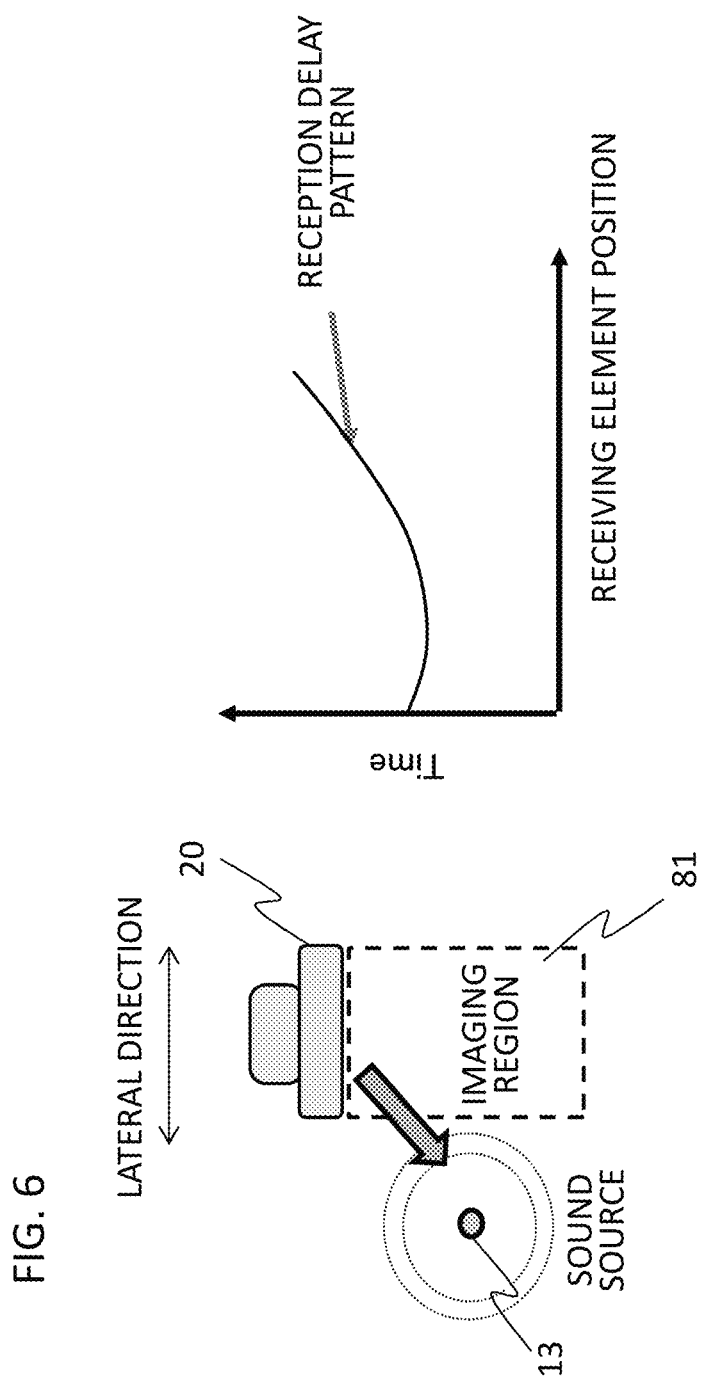
FIG. 6 is a diagram illustrating a relationship between an element position and a time difference.

Moreover, as illustrated in a graph included in FIG. 6, in a case where the PA signal generation source 13 is in a position deviating in the lateral direction from the diffracted wave region, the relationship between each element number of the array and the arrival time changes in a curved line from the right end toward the left end or from the left end toward the right end. It is possible to estimate a deviation in the lateral direction of the PA signal generation source 13 based on the curvature of the curved line. In this case, the analysis unit 353 can be configured not to perform calculation of the positional information but to perform a qualitative determination as to, for example, "far", "near", and "penetration into the diffracted wave region" with respect to the distance to the target based on an inclination in the graph representing a relationship between the element position and the arrival time and display a result of the determination on the display unit.

According to the present embodiment, in a case where the front edge position of the guide wire inserted into an object under examination is present outside the diffracted wave region of the ultrasonic probe and is away therefrom in the lateral direction, using a time difference between PA signals arriving at the respective elements of the ultrasonic probe enables estimating the position of the PA signal generation source, i.e., the position of the front edge of the guide wire.

Furthermore, in the case of generating a PA image of the PA signal generation source 13, the ultrasonic image forming unit 351 can sequentially generate the PA image before the PA signal generation source 13 enters the diffracted wave region 81, for example, at the same time as when the analysis mode is started, but can generate the PA image at a point of time when it is estimated that the PA signal generation source 13 has entered the diffracted wave region 81 from the distance of the PA signal generation source estimated by the analysis unit 353 in the analysis mode. Since the image of the PA signal generation source 13 present in the diffracted wave region 81 is a point-like image of the position of the PA signal generation source 13 in the diffracted wave region 81, superimposing the point-like image on an ultrasonic image of an imaging target tissue acquired in the imaging mode enables confirming the position of the PA signal generation source 13 in the tissue.

Modification Example of First Embodiment

While, in the first embodiment, the analysis unit 353 receives information about the light generation clock time from the light generation unit 15 to calculate the arrival time of the PA signal, even a system in which the photoacoustic device 10 (light generation unit 15) and the ultrasonic imaging device 30 do not perform exchange of signals is able to calculate a PA signal generation source using the receiving time of the PA signal.

Figure 7:
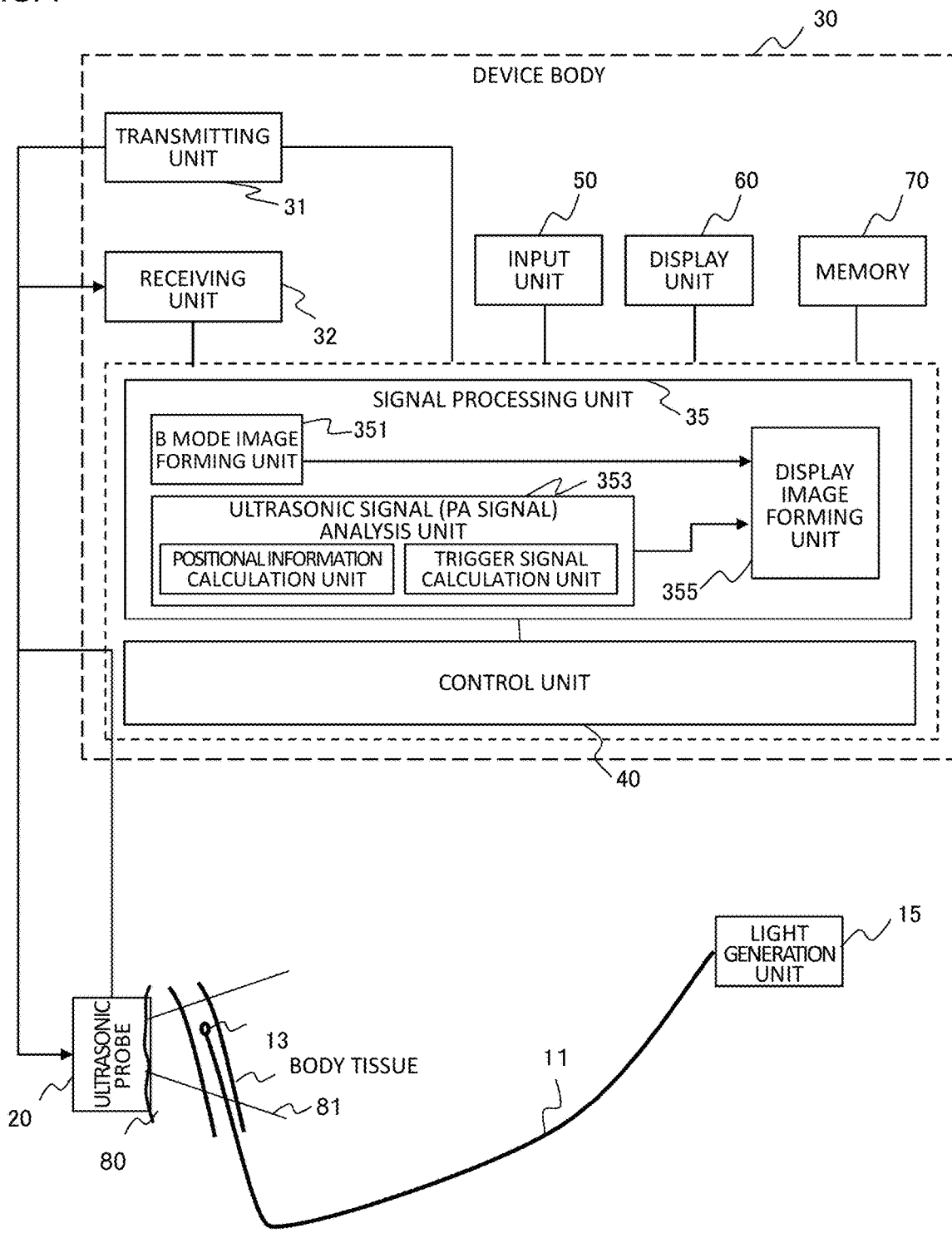
FIG. 7 is a diagram illustrating an overall outline of a treatment support system according to a modification example.

The system configuration in the present modification example is similar to the system configuration illustrated in FIG. 3 except that, as illustrated in FIG. 7, there is not a signal line via which to transmit a trigger signal from the light generation unit 15 to the ultrasonic imaging device 30. With regard to switching between the imaging mode and the analysis mode, for example, in a state in which the imaging mode is frozen, the photoacoustic device 10 is manually caused to operate to execute the analysis mode.

In the analysis mode, radiating laser light from the light generation unit 15 to cause a PA signal to be generated from the PA signal generation source 13 and receiving the PA signal by each element of the ultrasonic probe (1D array probe) are similar to those in the first embodiment. The analysis unit 353 calculates the position (xc) of the PA signal generation source 13 by the following formula (3) using information about the PA signal and receiving time acquired by the receiving unit 32 (PA signal detection unit).

$$\begin{Bmatrix} \frac{4\delta x}{C^2(t_3 - t_1)} x_2 - (t_3 + t_1) \\ \vdots \\ \frac{4\delta x}{C^2(t_{n+1} - t_{n-1})} x_n - (t_{n+1} + t_{n-1}) \\ \vdots \\ \frac{4\delta x}{C^2(t_N - t_{N-2})} x_n - (t_N + t_{N-2}) \end{Bmatrix} = \begin{Bmatrix} \frac{4\delta x}{C^2(t_3 - t_1)} & -2 \\ \vdots & \vdots \\ \frac{4\delta x}{C^2(t_{n+1} - t_{n-1})} & -2 \\ \vdots & \vdots \\ \frac{4\delta x}{C^2(t_N - t_{N-2})} & -2 \end{Bmatrix} \begin{pmatrix} x_c \\ t_F \end{pmatrix} \quad (3)$$

Formula (3) is a formula describing a simultaneous equations of formula (1) for every detection element by a matrix, and items with the respective same symbols as those in formula (1) have the respective same meanings. In formula (3), symbol "$t_F$" denotes the generation clock time of the PA signal and is an unknown number. Thus, this system of equations includes two unknown number "$t_F$" and "xc" (the distance in the lateral direction), and these unknown numbers are able to be obtained by solving an inverse problem of the matrix.

It is possible to calculate the distance "yc" in the depth direction by formula (4) similar to formula (2) using the numbers "$t_F$" and "xc" obtained in the above-mentioned way.

$$y_c = \sqrt{\frac{1}{N}\sum_{n=1}^{N} C^2(t_n + t_F)^2 - (x_n - x_c)^2} \quad (4)$$

According to the present modification example, even in a case where it is impossible to obtain the generation clock time of the PA signal by a trigger signal, it is possible to estimate the position of the PA signal generation source 13.

Furthermore, the position detection method is not limited to those in the above-described embodiment and modification example. For example, phasing processing can be performed in a region larger than an ordinary ultrasonic imaging region based on a beacon ultrasonic signal (PA signal) received by each element of the ultrasonic probe and a position at which beacon ultrasonic signals join together can be set as an identified position. Alternatively, coarse phase processing can be performed and a region in which signal strengths concentrate can be identified.

Second Embodiment

While, in the first embodiment and the modification example thereof, the position (the distance in the lateral direction) of the PA signal generation source 13 is estimated with use of a time difference between PA signals arriving at the respective elements of the ultrasonic probe, the analysis unit 353 in the present embodiment estimates a three-dimensional position of the PA signal generation source 13. Such an estimation includes a method of enabling grasping the three-dimensional position by an operation on the 1D ultrasonic probe 20A (a first method) and a method of using an ultrasonic probe 20B capable of grasping the three-dimensional position (a second method). In either case, with regard to the lateral direction, a method similar to that in the first embodiment is employed. First, the first method is described.

[First Method]

Figure 8:
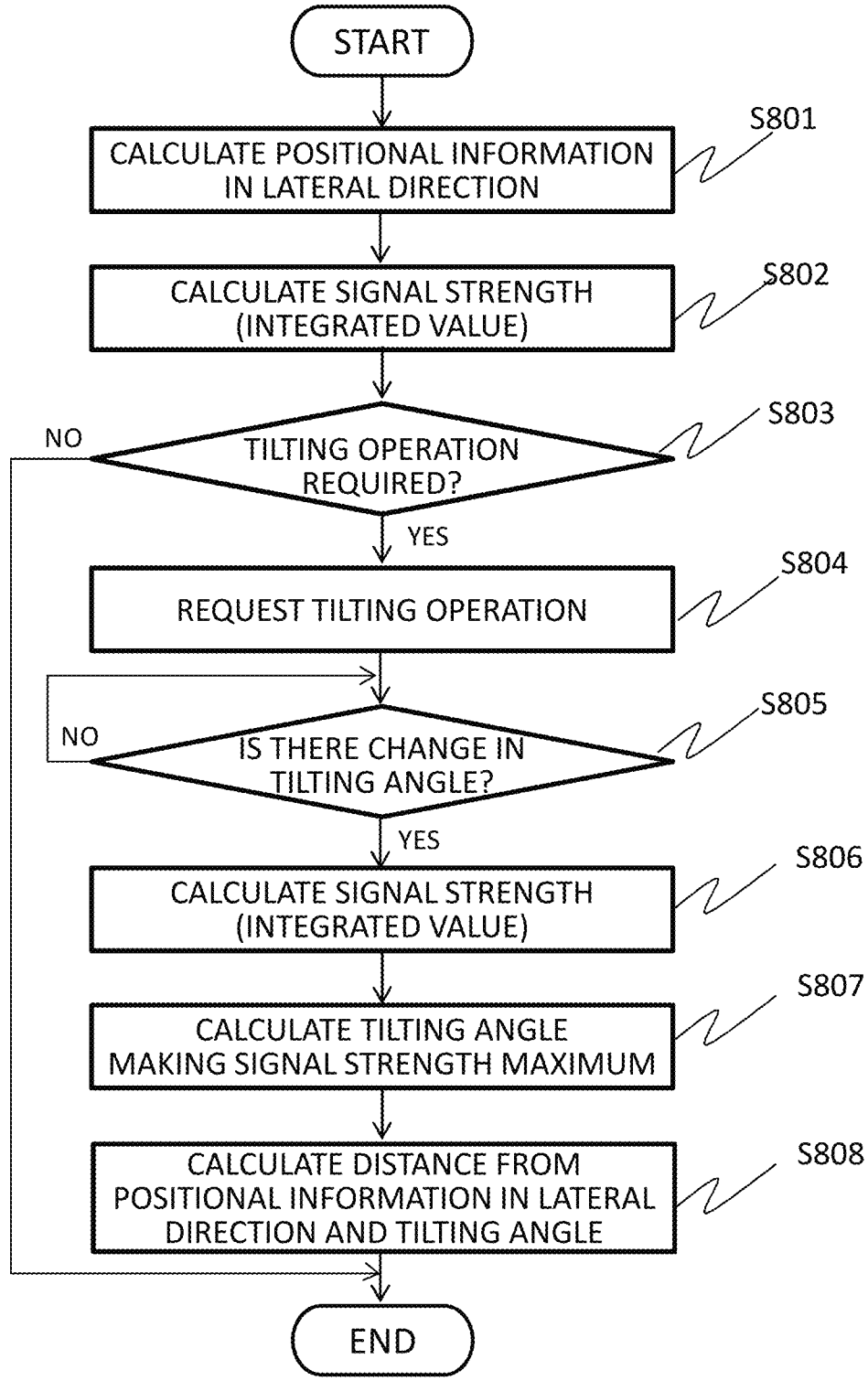
FIG. 8 is a chart illustrating a flow of processing which an analysis unit performs in a second embodiment.

FIG. 8 is a chart illustrating a flow of processing which is performed by the first method. As illustrated, even in the present embodiment, as with the first embodiment, first, the position (xc, yc) of the PA signal generation source 13 is calculated with use of an arrival time difference between PA signals to the respective elements (S801), and the receiving strength (integrated value) of PA signals received by the respective elements is also calculated (S802). Next, in a case where the strength of PA signals calculated in step S802 is lower than a predetermined threshold value (S803), information about that effect is sent to the display image forming unit 355. The display image forming unit 355 forms a GUI for prompting a tilting operation of the ultrasonic probe 20 and displays the GUI on the display unit 60 (S804).

Figure 9:
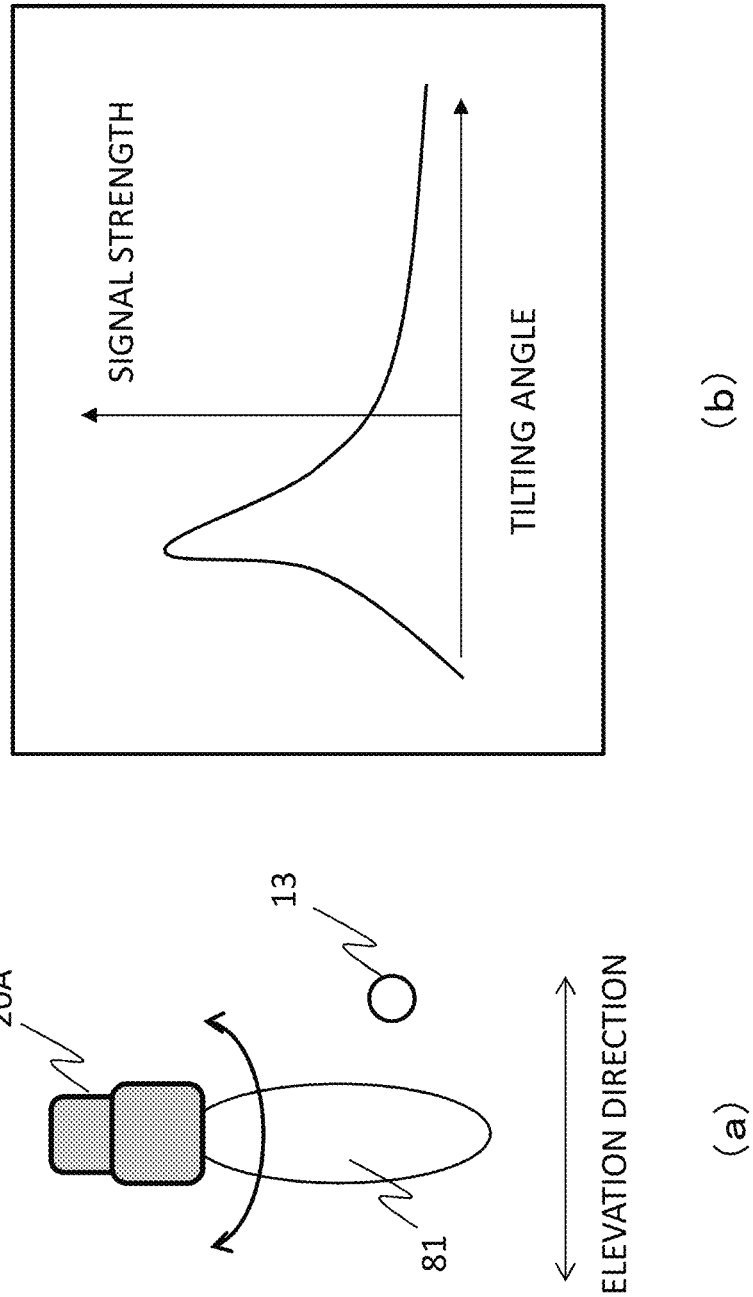
FIG. 9(a) is a diagram used to explain an operation for a tilting angle.
FIG. 9(b) is a graph illustrating a relationship between the tilting angle and the signal strength.

During this period, for example, the light generation unit 15 is continuing generation of pulsed laser light and the analysis unit 353 continues calculation of the signal strength in step S802 (S805 and S806). Then, when the user performs a tilting operation in the elevation direction (a direction perpendicular to the lateral direction) on the ultrasonic probe 20 according to the GUI displayed on the display unit 60, the sensitivity increases according to directivity and the signal strength also increases. FIG. 9 illustrates an example of a relationship between the tilting angle and the signal strength. FIG. 9(a) is a diagram of the 1D array ultrasonic probe 20A as viewed from the lateral direction, and FIG. 9(b) is a graph illustrating the relationship between the tilting angle and the signal strength. The analysis unit 353 detects such a change in signal strength caused by a change in tilting angle and obtains a tilting angle which makes the signal strength maximum (S807). This enables detecting the position of the PA signal generation source 13 in the elevation direction. In this case, since the position in the lateral direction of the PA signal generation source 13 is already known in step S801, using the known position and the tilting angle which makes the signal strength maximum enables geometrically calculating the position in the elevation direction (S808).

Furthermore, while, in the above description, a GUI for prompting the user to perform a tilting operation is displayed on the display unit 60, depending on users, there may be a case where the user habitually performs a tilting operation of the ultrasonic probe even in the absence of a prompt using, for example, a GUI. In such a case, displaying of the GUI (S803 and S804) can be omitted, and calculation of the signal strength in step S802 and detection of a tilting angle which makes the signal strength maximum in step S807 can be automatically performed simply in response to the user's operation to detect the position of the PA signal generation source 13.

[Second Method]

While the first method changes the tilting angle by operating the ultrasonic probe 20 to estimate the position of the PA signal generation source 13 being in a posit ion deviating from the imaging region (imaging cross-section) in the elevation direction, the second method uses a 2D array probe, in which elements are arranged in two-dimensional directions, to detect the position in two directions.

Detection of the position in two arrangement directions (a first direction and a second direction) is similar to the method of performing estimation of the position in the lateral direction using a time difference between elements in PA signal arrival time in the first embodiment, and the position in two directions is able to be calculated by formulae (1) and (2) or formulae (3) and (4) with use of a time difference between elements in the arrangement of elements in each direction. However, in these formulae, symbol "xc" is changed to read "the distance in the first direction of the ultrasonic probe" or "the distance in the second direction of the ultrasonic probe".

It is possible to calculate a three-dimensional position of the PA signal generation source 13 using the distances in the first and second directions obtained in the above-described way separately by calculation.

Furthermore, types of the ultrasonic probe 20 include, in addition to what is called a 2D array probe, a probe called a 1D three-row probe, in which about three rows of 1D arrays are arranged. In such an ultrasonic probe, the lateral direction (a direction in which the number of arranged elements is large) and the elevation direction (a direction in which the number of arranged elements is small) are differentiated from each other, and such an ultrasonic probe is used in a manner similar to the manner in which the 1D array is used. In a case where the ultrasonic probe 20 is a 1D three-row probe, the position of the PA signal generation source 13 in the elevation direction can be detected from the tilting angle based on a change in signal strength occurring when the tilting operation is performed, as with the 1D array. In that case, the positional information in the lateral direction can be calculated by using time differences between elements in the respective three rows of arrays and averaging them, and taking into consideration the distance relationship between an individual element and the position of a sound source enables increasing the position detection accuracy in the lateral direction.

Usually a blood vessel not only runs in a linear fashion within a tissue but also curves or branches. Accordingly, there is a case where it is impossible to accurately grasp its progress status only by using the position in the lateral direction. According to the present embodiment, acquiring the positional information in the elevation direction enables more accurately grasping the position of the ultrasonic wave generation source.

Moreover, in a case where the guide wire departs from an intended blood vessel and penetrates into a different blood vessel, it may be determined that the front edge position of the guide wire has entered the diffracted wave region from the distance in the lateral direction of the ultrasonic wave generation source estimated in the first embodiment. However, according to the present embodiment, acquiring the positional information not only in the lateral direction but also in the elevation direction enables estimating, for example, the guide wire departing from the intended blood vessel.

Third Embodiment

While, in the first embodiment and the second embodiment, the analysis unit 353 estimates the position of the ultrasonic wave generation source by using a difference between elements in a time taken for ultrasonic waves emitted from the ultrasonic wave generation source to arrive at the ultrasonic probe (an arrival time difference), in the present embodiment, the analysis unit 353 estimates the distance using features of an image occurring in a beacon ultrasonic image (PA image) according to the arrival time difference, specifically, using splits. Thus, in an ultrasonic imaging device in the present embodiment, the ultrasonic image forming unit 351 has a function of forming an image of the ultrasonic wave generation source using a beacon ultrasonic signal and the analysis unit 353 estimates the position of the ultrasonic wave generation source 13 from information about the image of the ultrasonic wave generation source generated by the ultrasonic image forming unit 351.

The influence of an arrival time difference occurring in a beacon ultrasonic image is described. While a PA signal is described as a typical example of a beacon ultrasonic signal, the same also applies to any other type of ultrasonic signal.

Since the PA signal is ultrasonic waves, phases of waves arriving at the respective elements differ for each element. The generation of a PA image is obtained by performing convolution of such out-of-phase signals. In this case, if being a signal generated from within the diffracted wave region, the PA signal is subjected to phasing to become a single image. But, an image of the PA signal generation source present in a position deviating from the diffracted wave region becomes blurred according to deviating from the diffracted wave region due to the influence of convolution (convolution effect). If deviating therefrom to a predetermined extent or more, the image of the PA signal generation source is vertically split (separated) and divided into a plurality of images. FIG. 10 illustrates a PA image in which splits have occurred. FIG. 10(a) is a diagram illustrating a plurality of positions (four positions) of the PA signal generation source 13, which differ in the distance to the diffracted wave region 81, and FIG. 10(b) is a diagram illustrating PA images in the respective positions. As illustrated, with regard to splits, as the distance from the diffracted wave region is larger, the number of splits increases and an interval between split images becomes wider.

When using an interval between splits of the PA image, the analysis unit 353 in the present embodiment calculates the position of the PA signal generation source by the following formulae (5) and (6).

$$y_c = \frac{D_d^2 - D_u^2}{2d} \quad (5)$$

where
$D_d^2$: the distance (depth) to the lower point of the split points, and
$D_u^2$: the distance (depth) to the upper point of the split points.

$$z_c = \sqrt{\left(y_c - \frac{d}{2}\right)^2 - D_u^2} \quad (6)$$

The symbols in formulae (5) and (6) are as follows:
Yc: the position of the sound source in the lateral direction,
Zc: the position of the sound source in the elevation direction, and
d: the aperture diameter in the minor axis (elevation direction).

Determining the degree of proximity (degree of separation) of the guide wire to the diffracted wave region based on the distances calculated in the above-mentioned way to display the determined degree is similar to that in the first embodiment. Moreover, the analysis method in the present embodiment is able to be combined with the analysis performed in the first embodiment or the second embodiment, and this enables presenting more detailed information about the guide wire position to the user. Furthermore, while, with regard to a PA image used for analysis, the PA image itself can be displayed on the display unit 60, the PA image is also able to be displayed in superimposition on an ultrasonic image acquired in the imaging mode. Since, in a case where the PA signal generation source 13 is away from the diffracted wave region, the image of the PA signal generation source 13 superimposed on the ultrasonic image is displayed at a portion deep in depth of the ultrasonic image, the user is able to confirm the manner in which the PA signal generation source comes close, by looking at splits of point images appearing at the deep portion of an image of the tissue.

According to the present embodiment, using splits appearing in a PA image enables visually confirming a proximity status to the diffracted wave region without difficulty and also estimating the distance thereto.

Modification Example of Third Embodiment

While the third embodiment calculates the position of the PA signal generation source from splits appearing in a PA image, in this case, information about a direction in which the PA signal generation source proceeds to the diffracted wave region is unable to be obtained. The present modification example employs an asymmetric array structure for the ultrasonic probe and also acquires information about the direction by detecting the effect of asymmetricity on splits.

Figure 11:
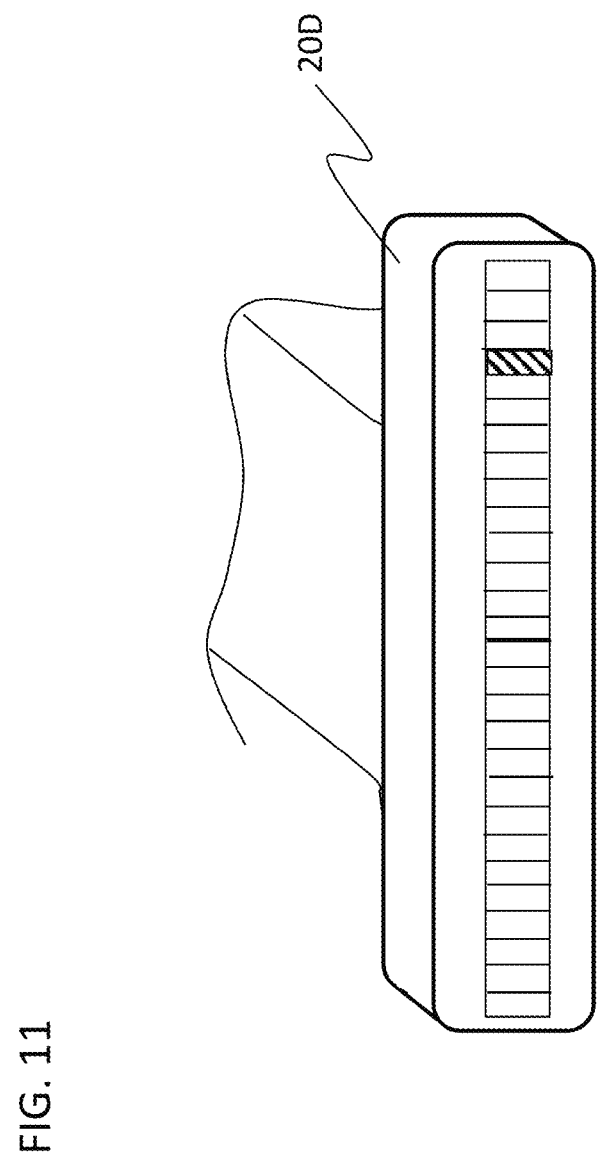
FIG. 11 is a diagram illustrating an example of an asymmetric ultrasonic probe which is used in a modification example of the third embodiment.

FIG. 11 illustrates an example of the asymmetric array structure. This ultrasonic probe 20D is a 1D array probe, and a part (for example, one element) of elements arranged on one side of the center in the element arrangement direction is made inoperative in the analysis mode. Control to make one element inoperative can be performed by the control unit 40, which receives a trigger signal for communicating radiation of laser light from the light generation unit 15, or can be performed at the time of mode switching in a case where the control unit 40 controls switching between the imaging mode and the analysis mode.

Even in this ultrasonic probe, when the PA signal generation source 13 is away from the diffracted wave region, splits occur in a PA image, and the number of splits increases as the distance becomes larger. Here, in a case where the ultrasonic probe has asymmetricity, asymmetricity also appears vertically in the splits. For example, in a case where, as illustrated in FIG. 12, there is one inoperative element out of the arranged elements, the image of a PA signal generation source 13A present at a position deviating from the diffracted wave region of the ultrasonic probe is split into a plurality of images. Here, one of a plurality of images obtained by splitting and arranged side by side vertically is lost and the image loss position differs depending on whether the inoperative element is present on the left side or on the right side. Accordingly, the shape (asymmetricity) of splits is able to be used to estimate the position of the PA signal generation source relative to the diffracted wave region, i.e., on which side the front edge of the guide wire is present with respect to the target tissue included in the displayed ultrasonic image.

According to the present modification example, it is possible to present direction information in addition to positional information estimated by the analysis unit in the third embodiment. Furthermore, in the above description, a case where one of elements is made inoperative as a means for making an asymmetric array structure has been described. However, one element can be made physically inoperative by, for example, attaching a seal member made from a material which does not transmit ultrasonic waves to the surface (contact side) of the element. Even in this case, as long as the number of elements to be sealed is about one, the influence on the imaging mode can be ignored.

Fourth Embodiment

The present embodiment is characterized in that the ultrasonic probe 20 is not operated by the user but is operated by a robot arm.

Figure 13:
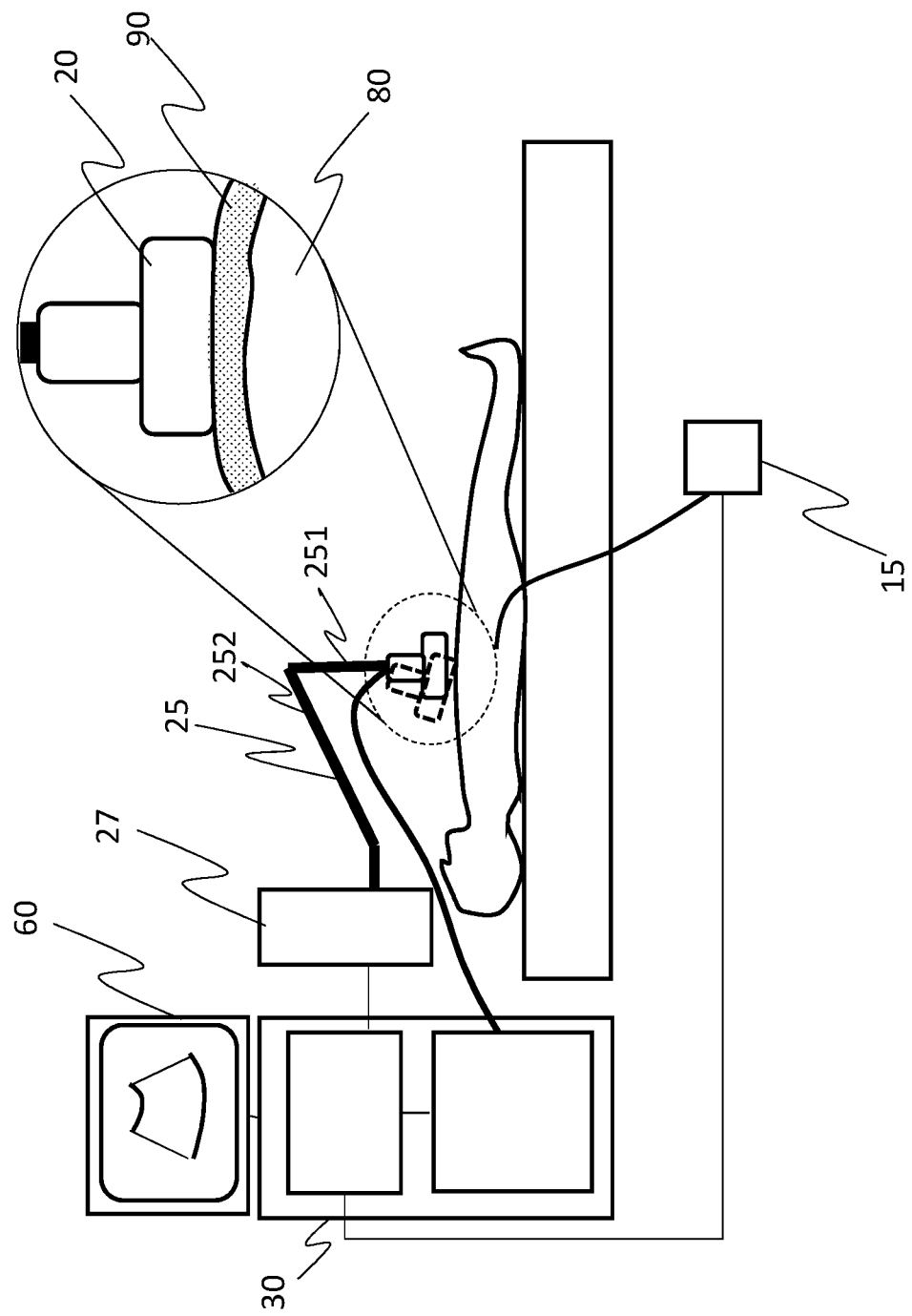
FIG. 13 is a diagram illustrating an overall outline of an embodiment of a treatment support system according to a fourth embodiment.

FIG. 13 illustrates an example of a treatment support system 100A configured to implement the present embodiment. In FIG. 13, the same elements as the elements illustrated in FIG. 1 are assigned the respective same reference characters, and any repeated description thereof is omitted. The illustrated treatment support system includes a robot arm 25, on which the ultrasonic probe 20 is mounted, and a drive device 27 for the robot arm 25.

The robot arm 25 includes, although not illustrated, for example, a supporting unit, which supports the ultrasonic probe 20 in an attachable and detachable manner, an arm member, which is coupled to the supporting unit in such a way as to be able to rotate in an axial direction and has a plurality of arms link-coupled to each other, and a mechanical unit, which drives the arm member in the vertical direction and in the horizontal direction, and moving these mechanical units enables bringing the ultrasonic probe 20 into contact with an object under examination 80, rotating or translating the ultrasonic probe 20 while keeping the ultrasonic probe 20 in contact with the object under examination 80, or changing the tilting angle thereof. As illustrated while being circled in the figure, a gel-like sheet member 90 is arranged between the ultrasonic probe 20 and the surface of the object under examination 80.

The drive device 27 includes, for example, a motor which drives the mechanical units of the robot arm 25, is connected to the control unit 40 of the ultrasonic imaging device 30, and operates under the control of the control unit 40.

An operation of this support system 100A is essentially similar to that in the first method of the above-described second embodiment, and acquires two-dimensional information by changing the orientation of the ultrasonic probe. While, in the first method of the second embodiment, the tilting angle is changed by a manual operation, in the present embodiment, the tilting angle is varied by controlling the robot arm mounted to the probe.

Figure 14:
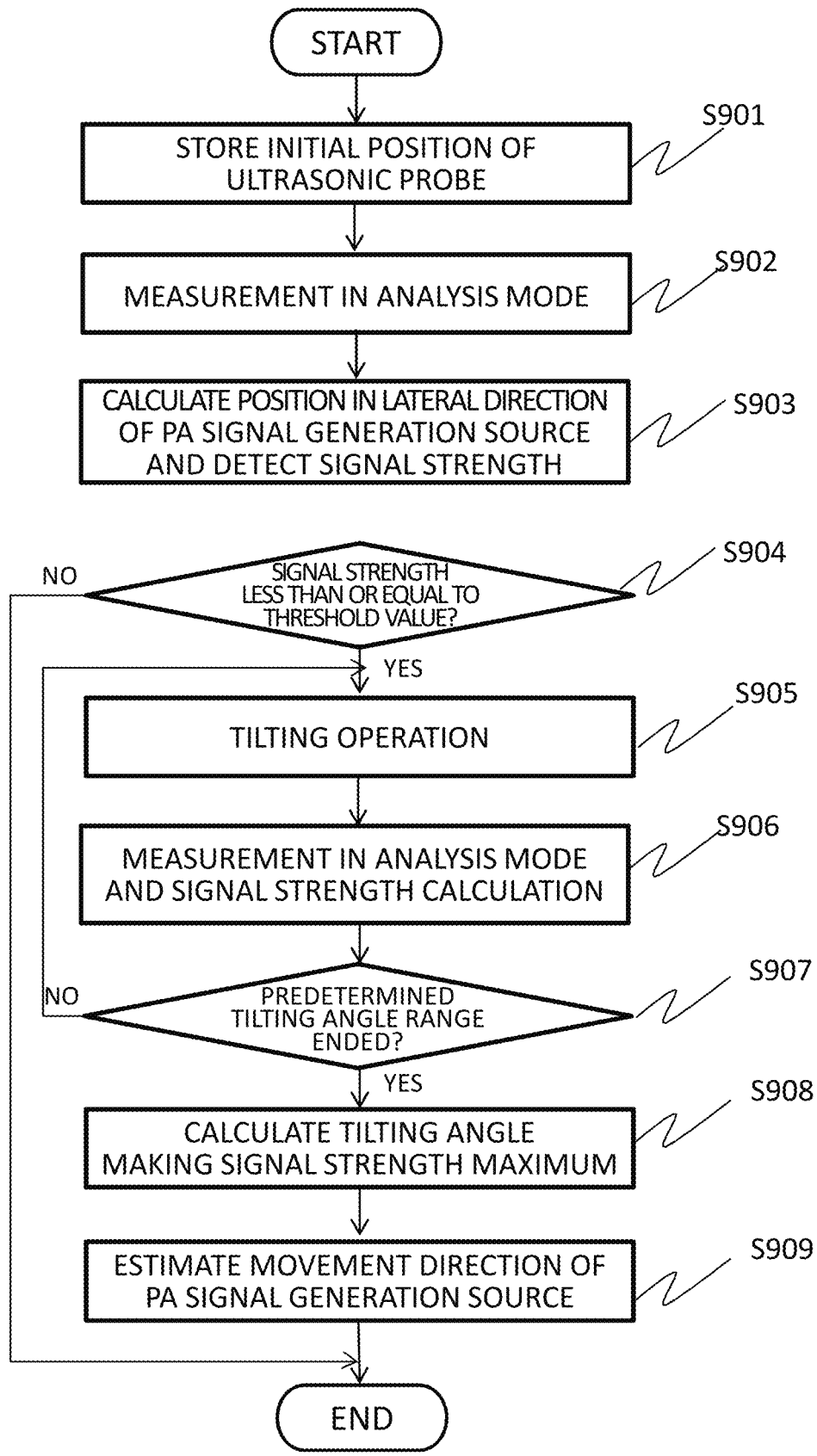
FIG. 14 is a chart illustrating a flow of processing which a control unit and an analysis unit in the fourth embodiment perform.

An example of an operation in the analysis mode in the present embodiment is described with reference to FIG. 14.

When, as a premise, the position (initial position) of the ultrasonic probe 20 in which an imaging site intended in the imaging mode is set as an imaging region is determined, the analysis mode is started at the determined position. Information about the initial position is stored in, for example, the memory 70 (S901). In the analysis mode, as with the first embodiment, laser light is radiated from the light generation unit 15, a PA signal is generated from the PA signal generation source, and the generated PA signal is received by the ultrasonic probe 20 (S902). The analysis unit 353 estimates the distance of the PA signal generation source using a PA signal arrival time difference at the respective elements of the ultrasonic probe 20 and stores the signal strength thereof (stores it in the memory) (S903).

The control unit 40 determines whether the signal strength is less than or equal to a predetermined threshold value (S904), and, if the signal strength is less than or equal to the threshold value, the control unit 40 sends a control signal to the drive device 27 to, for example, perform control to change the tilting angle by rotating a supporting unit 251 supporting the ultrasonic probe 20 with respect to an arm portion 252 (S905) and performs measurement in the analysis mode (S906). For example, the control unit 40 repeats changing of the tilting angle within a previously set predetermined tilting angle range and measurement in the analysis mode (S907), and acquires information about signal strengths for a plurality of tilting angles including plus and minus angles. The analysis unit 353 calculates a tilting angle which makes the signal strength maximum out of the signal strengths for the respective tilting angles (S908), and determines, based on the calculated tilting angle, on which side in the elevation direction the front edge of the guide wire is present with respect to the imaging region (S909). Moreover, the analysis unit 353 can estimate the accurate distance of the front edge of the guide wire (the distance to the diffracted wave region) by using the tilting angle which makes the signal strength maximum and the positional information in the lateral direction estimated in step S903.

When the analysis mode is switched to the imaging mode, the control unit 40 controls the drive mechanism 27 in such a way as to return the position of the ultrasonic probe 20 to the initial position stored in the memory 70 in step S901, and then executes the imaging mode.

According to the present embodiment, as with the second embodiment, it is possible to acquire three-dimensional positional information about the front edge of the guide wire and, at that time, it is possible to present the accurate position of the front edge of the guide wire without giving the operator a lot of trouble. This enables the operator to concentrate on insertion of the guide wire and subsequent transcatheter treatment, so that a high support effect can be obtained.

Furthermore, even in the present embodiment, the estimation of the distance of the PA signal generation source can be directly calculated from a PA signal arrival time difference for the elements as with the first embodiment, or can be calculated from an interval of splits occurring in a PA image as with the third embodiment.

Embodiment of Displaying

Next, an embodiment of a method of presenting the position and direction of the PA signal generation source calculated and estimated by the analysis unit in each of the above-described embodiments (processing which is performed by the display image forming unit) is described.

Display Example 1

Figure 15:
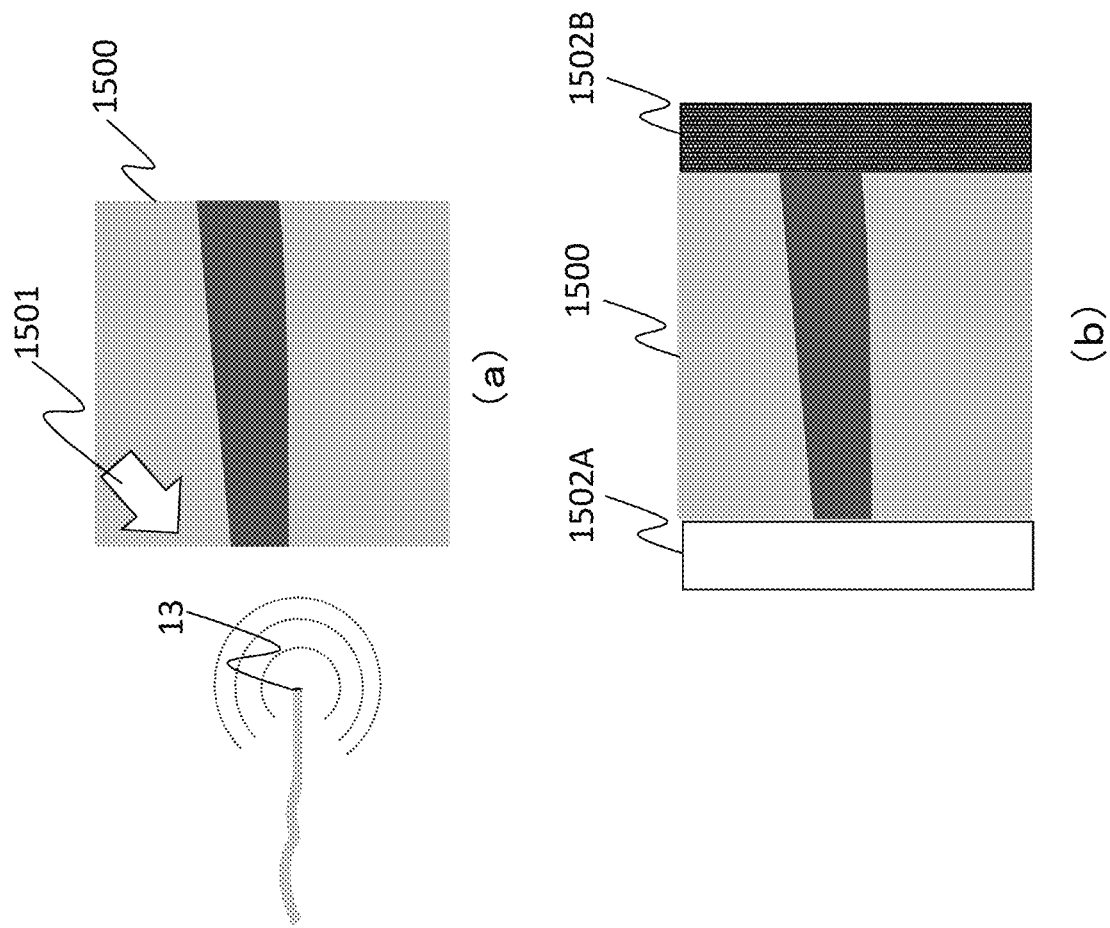
FIGS. 15(a) and 15(b) are diagrams each illustrating an example of display for displaying a direction as positional information about the front edge of a guide wire.

The present display example presents most important information in a support for surgery using a guide wire, such as the direction in which the guide wire is coming close to a region being observed with an ultrasonic image and how the guide wire has come close to the region. FIG. 15 illustrates an example indicating direction information.

In the example illustrated in FIG. 15(a), an arrow (beacon) 1501 indicating from where the guide wire is coming close is displayed on a screen 1500 for displaying an ultrasonic image including a tissue of the object under examination. This display enables the user to know that the guide wire is coming close from the direction indicated by the arrow. When the front edge of the guide wire has entered the imaging region of the displayed ultrasonic image, the ultrasonic image (PA) of the PA signal generation source 13 can be displayed in superimposition on the ultrasonic image (not illustrated).

In the example illustrated in FIG. 15(b), direction display portions 1502A and 1502B for indicating the guide wire coming close are provided on both sides of a screen for displaying an ultrasonic image. For example, when the guide wire is coming close from the left side of the displayed ultrasonic image, the direction display portion 1502A on the left side is lighted up and becomes bright. The direction display portion 1502B on the right side remains dark. This enables the user to know that the guide wire is coming close from the side on which the direction display portion is lighted up. In this case, the brightness of the direction display portion on the side where the guide wire is present can be varied according to the distance of the guide wire. For example, when the guide wire is present at a position far from the diffracted wave region, the direction display portion is not lighted up, and, when the guide wire has come close to a predetermined distance, the direction display portion is lighted up at a low brightness. Then, as the distance to the diffracted wave region becomes shorter, the brightness of the direction display portion is increased.

Moreover, in addition to displaying for presenting the direction illustrated in FIG. 15, for example, positional information about the guide wire calculated in the first to third embodiments can be additionally displayed at, for example, an end portion of the display screen for an ultrasonic image. The positional information can be a numerical value of, for example, the position of the PA signal generation source 13 calculated in the first embodiment or the distance to a specific tissue (for example, a target) on an ultrasonic image, or can be a qualitative displaying manner such as "far (200 mm or more)" or "near (100 mm or less)". Since the positional information estimated by the analysis unit varies due to the analysis mode being repeated, displaying is updated in conformity with such variation.

According to the present display embodiment, it is possible to present, on an ultrasonic image, the direction and proximity of the guide wire, which are most important information, in performing a support for surgery using the guide wire. This enables the operator to, while focusing on insertion of the guide wire, visually confirm how the insertion is going.

Display Example 2

In the present display example, in a case where three-dimensional information about the PA signal generation source has been acquired, the position of the PA signal generation source is displayed on an ultrasonic three-dimensional image.

Figure 16:
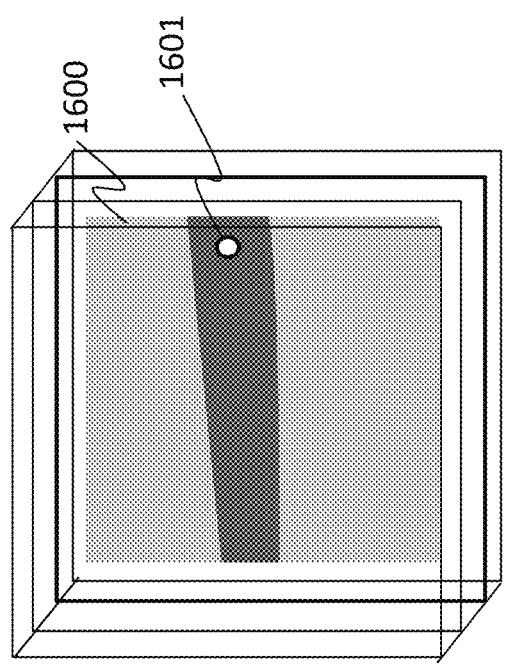
FIG. 16 is a diagram illustrating an example of display for a front edge position of the guide wire in a three-dimensional image.

In a case where the 2D array probe 20B has been used or in a case where imaging has been performed by operating the 1D array probe in a sweeping manner in the elevation direction, three-dimensional ultrasonic image data is obtained. The display image forming unit 355 generates a rendering image 1600 such as that illustrated in FIG. 16 with use of the three-dimensional image data, and superimposes a predetermined mark image 1601 on a position corresponding to the position of the PA signal generation source in the rendering image. The mark is not particularly limited, and can be a spherical mark representing the PA signal generation source or can be an arrow mark indicating the movement direction of the PA signal generation source. Additionally, the mark can be a linear mark obtained by connecting the time-varying positions of the PA signal generation source.

Display Example 3

Figure 17:
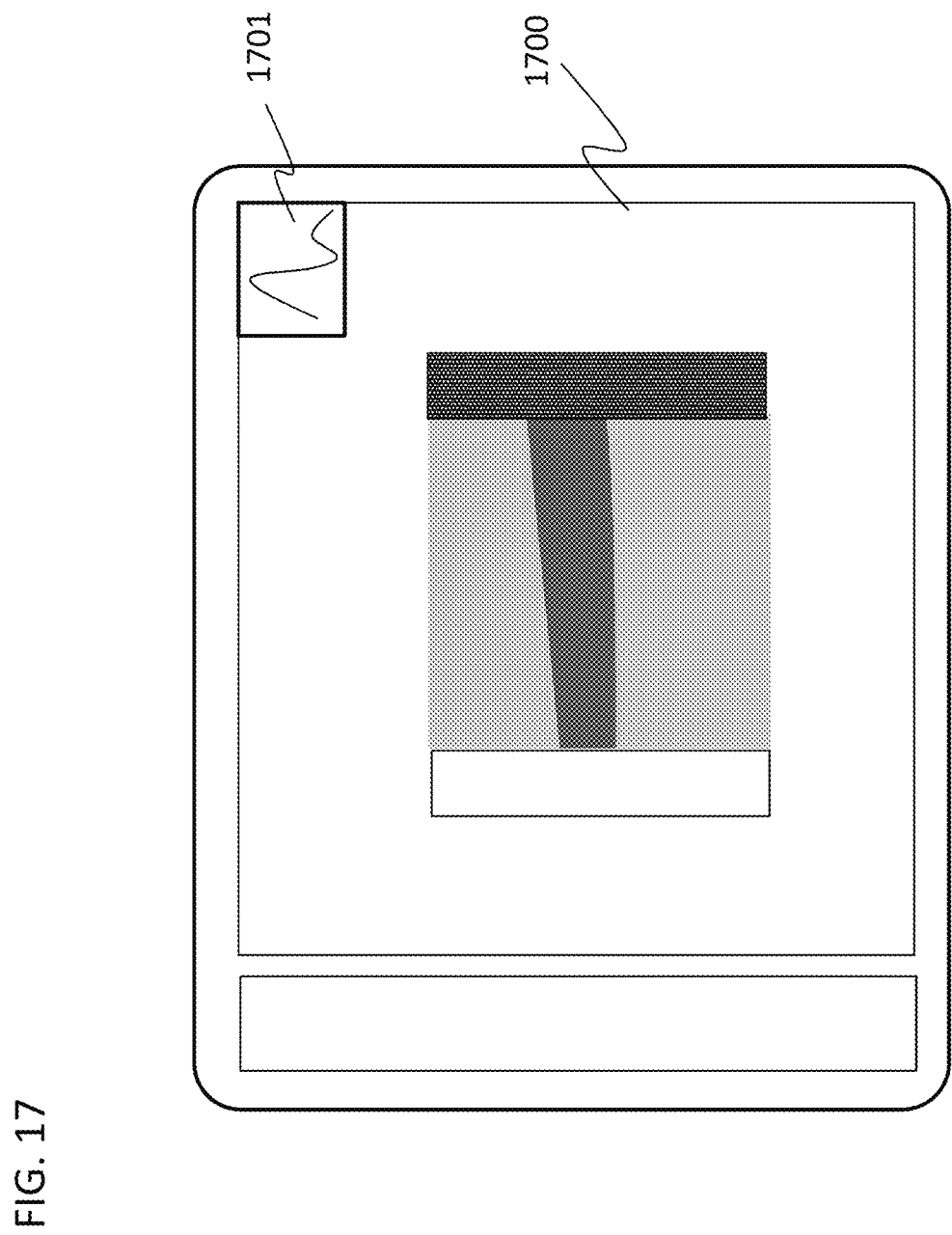
FIG. 17 is a diagram illustrating an example of display for signal strength change.

The present embodiment is configured to provide a signal strength display portion, which displays the signal strength of the received PA signal, in a screen for displaying an ultrasonic image. FIG. 17 illustrates a display example. In this display example, a display portion 1701 for the PA signal strength varying from moment to moment is provided at a position which does not overlap an image in a screen 1700, so that the temporal variation of the signal strength is displayed in a graph-like manner. The signal strength of a PA signal varies according to the distance of the PA signal generation source 13 from the ultrasonic probe (the distance from the diffracted wave region) and, moreover, also varies when the tilting angle of the ultrasonic probe is changed, as with the first method of the second embodiment and the fourth embodiment.

In the present embodiment, the display image forming unit 355 uses information about time-varying variations of the signal strength received from the analysis unit 353 to create a graph with, for example, the horizontal axis set as time and the vertical axis set as signal strength, and displays the created graph on the signal strength display portion 1701 in the display screen. This graph is updated each time measurement in the analysis mode is repeated. In the case of changing the tilting angle, the display image forming unit 355 can create a graph with the horizontal axis set as tilting angle and display the created graph.

According to the present embodiment, it is possible to view the movement status of the guide wire as a variation in signal strength. Furthermore, in addition to displaying of a graph indicating the signal strength, displaying corresponding to another display example can be performed together.

While various embodiments of the ultrasonic imaging device and the transcatheter treatment support system according to the present invention have been described above, the described embodiments can be combined as appropriate unless a technical contradiction arises, and such a combination is also encompassed in the present invention.

DESCRIPTION OF REFERENCE NUMERALS AND SIGNS

10: photoacoustic device, 11: wire, 12: optical fiber, 13: PA signal generation source, 15: light generation unit, 20: ultrasonic probe, 30: ultrasonic imaging unit (ultrasonic imaging device), 31: transmitting unit, 32: receiving unit, 35: signal processing unit, 40: control unit, 50: input unit, 60: display unit, 70: memory, 80: object under examination, 81: imaging region (diffracted wave region), 351: ultrasonic image forming unit, 353: PA signal analysis unit, 355: display image forming unit.

The invention claimed is:

1. An ultrasonic imaging device characterized by comprising:
an imaging unit that transmits a beam-formed transmission ultrasonic signal to an object under examination via an ultrasonic probe, receives a reflective ultrasonic signal from a region onto which the ultrasonic signal has been radiated, and captures an ultrasonic image of the region; and
a computer coupled to the imaging unit,
wherein the ultrasonic probe includes a plurality of elements, and
wherein the computer programmed to:
receive, via the ultrasonic probe, ultrasonic waves generated an ultrasonic wave generation source inserted into an inside of the object under examination and analyze the received ultrasonic waves,
use ultrasonic waves acquired by varying a tilting angle in an elevation direction of the ultrasonic probe to acquire a relationship between the tilting angle and a signal strength of the ultrasonic waves and calculate a distance in an elevation direction of the ultrasonic wave generation source based on the relationship, and
estimate a position of the ultrasonic wave generation source, which is present at a position laterally deviating from the region, based on a difference between respective receiving times of ultrasonic waves which are respectively received by the plurality of elements of the ultrasonic probe, and based on the calculated distance in the elevation direction.

2. The ultrasonic imaging device according to claim 1, wherein computer is programmed to estimate the position of the ultrasonic wave generation source with respect to the region based on a time difference between arrival times of the ultrasonic waves at the respective elements.

3. The ultrasonic imaging device according to claim 2, wherein the computer is programmed to receive, from a light generation source that generates a light signal for causing the ultrasonic wave generation source to generate ultrasonic waves, information about a generation clock time of the light signal, and calculates the time difference between arrival times based on the generation clock time.

4. The ultrasonic imaging device according to claim 2, wherein the computer is programmed to estimate the time difference between arrival times and the position of the ultrasonic wave generation source by performing analysis based on simultaneous equations using a time difference between the receiving times of ultrasonic waves and a distance between the respective elements.

5. The ultrasonic imaging device according to claim 1, wherein the ultrasonic probe is a 1D array probe in which the plurality of elements are arranged in a one-dimensional direction.

6. The ultrasonic imaging device according to claim 1, wherein the ultrasonic probe is a 2D array probe in which the plurality of elements are arranged in two-dimensional directions, and
wherein the computer is programmed to use a first ultrasonic wave which a group of elements arranged in a first direction receives to calculate a distance in the first direction of the ultrasonic wave generation source, and use a second ultrasonic wave which a group of elements arranged in a second direction perpendicular to the first direction receives to calculate a distance in the second direction of the ultrasonic wave generation source.

7. The ultrasonic imaging device according to claim 5, wherein the ultrasonic probe is a 1D array probe including the plurality of element rows arranged in a one-dimensional direction.

8. The ultrasonic imaging device according to claim 1, wherein the computer is programmed to form an ultrasonic image using an ultrasonic signal received by the ultrasonic probe, and
generate an image of the ultrasonic wave generation source using the ultrasonic waves generated from the ultrasonic wave generation source.

9. The ultrasonic imaging device according to claim 1, further comprising:
a display device coupled to the computer,
wherein the computer is programmed to:
cause the ultrasonic image acquired by the imaging unit to be displayed on the display device, and
cause the information about the position of the ultrasonic wave generation source estimated to be displayed on the display device simultaneously with the ultrasonic image.

10. The ultrasonic imaging device according to claim 9, wherein the information to be displayed on the display device is information for making at least one of a direction and a position of the ultrasonic wave generation source with respect to the region recognizable.

11. The ultrasonic imaging device according to claim 1, further comprising:
a robot arm, coupled to the computer, that automatically operates the ultrasonic probe; and
a controller that controls motion of the robot arm,
wherein the controller is configured to control a tilting operation of the ultrasonic probe using a result of analysis performed by the computer.

12. An image processing method that receives reflective waves of an ultrasonic signal radiated onto an object under examination via an ultrasonic probe, which includes a plurality of elements, generates an ultrasonic image of a region onto which the ultrasonic signal has been radiated, receives, via the ultrasonic probe, ultrasonic waves generated by an ultrasonic wave generation source inserted into an inside of the object under examination, detects a position of the ultrasonic wave generation source with respect to the region with use of the received ultrasonic waves, and displays the detected position together with the ultrasonic image, the image processing method characterized by comprising:

using ultrasonic waves acquired by varying a tilting angle in an elevation direction of the ultrasonic probe to acquire a relationship between the tilting angle and a signal strength of the ultrasonic waves and calculate a distance in an elevation direction of the ultrasonic wave generation source based on the relationship; and calculating a position of the ultrasonic wave generation source to the region based on a difference between respective arrival times of ultrasonic waves at respective elements of the ultrasonic probe or an interval between splits appearing in an image of the ultrasonic wave generation source generated from the ultrasonic waves, and based on the calculated distance in the elevation direction.

* * * * *